(12) United States Patent
Wurst et al.

(10) Patent No.: US 8,952,095 B2
(45) Date of Patent: Feb. 10, 2015

(54) CROSS-LINKING AGENTS FOR HYDROGELS THAT CONTAIN CLEAVABLE PEPTIDES AND SHORT-CHAIN POLYMERS

(75) Inventors: Helmut Wurst, Pfullingen (DE); Karima Larbi, Singapore (SG); Markus Herrmann, Reutlingen (DE)

(73) Assignee: CELLENDES GmbH, Reutlingen (DE)

( * ) Notice: Subject to any disclaimer, the term of this patent is extended or adjusted under 35 U.S.C. 154(b) by 152 days.

(21) Appl. No.: 13/574,316

(22) PCT Filed: Feb. 4, 2011

(86) PCT No.: PCT/EP2011/000503
§ 371 (c)(1),
(2), (4) Date: Oct. 29, 2012

(87) PCT Pub. No.: WO2011/103961
PCT Pub. Date: Sep. 1, 2011

(65) Prior Publication Data
US 2013/0052736 A1 Feb. 28, 2013

(30) Foreign Application Priority Data
Feb. 23, 2010 (DE) .......................... 10 2010 009 876

(51) Int. Cl.
*A61K 47/48* (2006.01)
*C12N 5/00* (2006.01)

(52) U.S. Cl.
CPC ..... *A61K 47/48338* (2013.01); *A61K 47/48784* (2013.01); *C12N 5/0068* (2013.01); *C12N 2533/50* (2013.01); *C12N 2537/10* (2013.01)
USPC ............................. 525/54.1; 525/408; 525/430

(58) Field of Classification Search
CPC ........... C08G 65/2615; C08G 65/2621; C08G 65/2633; C08G 69/10; C08G 69/40

USPC ........................................ 525/54.1, 408, 430
See application file for complete search history.

(56) References Cited

FOREIGN PATENT DOCUMENTS

WO 2007/083870 A1 7/2007

OTHER PUBLICATIONS

English Translation of the International Preliminary Report on Patentability (Chapter II), IPEA/EP, published Sep. 3, 2012.
S. Kim & K. Healy: "Synthesis and characterization of injectable poly (N-isopropylacrylamide-co-acrylic acid) hydrogels with proteolytically degradable cross-links", Biomacromolecules., vol. 4, No. 5, 2003, pp. 1214-1223, XP002635236, ACS, Washington, DC., ISSN: 1525-7797, the whole document.
Database Biosis [Online] Biosciences Information Service, Philadelphia, PA, US; Dec. 2007, Khelfallah Nawel S et al: "Design, synthesis, and degradation studies of new enzymatically erodible poly(hydroxyethyl methacrylate)/poly(ethylene oxide) hydrogels", XP002635255, Database accession No. PREV200800472961, abstract.
N S Khelfallah et al: "Synthesis of a new PHEMA-PEO enzymatically biodegradable hydrogel", Macromolecular Rapid Communications., vol. 27, No. 13, Jul. 5, 2006, pp. 1004-1008, XP002635237, Weinheim (DE)., the whole document.
Nagase, H. and Fields, G. B., (1996), Human matrix metalloproteinase specificity studies using collagen sequence-based synthetic peptides. Biopolymers, 40: 399-416. Doi: 10.1002/(SICI)1097-0282(1996) 40:4,399::AID-BIP5.3.0.CO;2-R (abstract).
International Search Report and Written Opinion of the ISA, ISA/EP, Rijswijk, NL, mailed Jun. 15, 2011.

*Primary Examiner* — Robert Jones, Jr.
(74) *Attorney, Agent, or Firm* — Harness, Dickey & Pierce, P.L.C.

(57) ABSTRACT

A peptide cross-linking agent in the form of a linear molecule has a molecular mass of 3 to approximately 60 kDa. The peptide cross-linking agents are used for cross-linking functionalized polymers to form hydrogels having two or more components.

17 Claims, 8 Drawing Sheets

CROSS-LINKING AGENTS FOR HYDROGELS THAT CONTAIN CLEAVABLE PEPTIDES AND SHORT-CHAIN POLYMERS

CROSS-REFERENCE TO RELATED APPLICATIONS

This application is a 371 U.S. National Stage of International Application No. PCT/EP2011/000503, filed Feb. 4, 2011, which claims priority to German Patent Application No. 10 2010 009 876.0, filed Feb. 23, 2010. The disclosures of the above applications are entirely incorporated herein by reference.

FIELD

The invention relates to biocompatible two-component or multicomponent hydrogels especially for embedding and culturing biological cells and/or as a pharmaceutical formulation as well as novel peptide crosslinking agents for crosslinking bond functionalized polymers to form such hydrogels. The invention therefore provides a linear molecule which has a molecular weight of approx. 3 kDa to approx. 60 kDa and has a bond function in the area of the molecular termini and can crosslink complementary bond functionalized polymers.

BACKGROUND

Polymer hydrogels for use as biocompatible or biomimetic substrates, in particular for culturing biological cells and tissues are known. Two-component or multicomponent gels are usually synthesized from a high-molecular polymer as the first component and a low-molecular crosslinking agent as the second component. Known two-component or multicomponent hydrogels with peptide crosslinking have, for example, multi-arm macromolecular structures of polyethylene glycol (PEG), which are crosslinked via short linear peptides. The crosslinking agent molecules are known to have a linear molecular structure. They have at least two, preferably terminal, bond functions of a first type, for example, a thiol function, which conjugate with complementary bond functions of a second type, for example, a maleimide function, of the polymers to be crosslinked, for example, PEG, PVA, albumin or dextran, thus forming a crosslinked gel.

Such hydrogels may also be designed to be biodegradable by the metabolic activity of the cells cultured therein or cleavable by other time-dependent processes. This cleavability allows the hydrogel matrix to be replaced by an extracellular matrix (ECM) formed by the cells themselves in the course of culturing and/or the migration of cells into the hydrogels. To achieve biodegradability or cleavability of the hydrogels, it is known that they can be produced with peptide crosslinking agents composed of linear peptides. The peptides are cleavable by bioactive molecules in particular enzymes such as peptidases or proteinases, for example, matrix metalloproteinases (MMP). The hydrogel structure is dissolved again by intramolecular cleavage of the crosslinking agent.

The main disadvantage of known hydrogels is that the concentration of the crosslinking agent peptides must be high, i.e., more than 10 mmol/liter in any case, usually 20 mmol/liter or more, to form a stable hydrogel which is suitable in particular for cell culturing. Known crosslinking agent peptides are expensive to produce. The high concentration of crosslinking agent also has a negative effect on the possibility of adding other soluble components to the hydrogel during production and reduces the water content of the hydrogel. Such known crosslinked hydrogels therefore need to be improved.

SUMMARY

The object of the present invention is to improve upon peptide crosslinking agents for producing multicomponent hydrogels. A technical problem on which the invention is based is to provide means and methods so that the formation of hydrogel can take place at a lower crosslinking agent concentration than was possible in the past.

To completely solve the technical problem, the present invention thus makes available a novel peptide crosslinking agent molecule having at least one bond function on or in the area of the respective molecular termini for crosslinking of complementary bond functionalized polymers for use as the polymer crosslinking agent for two-component or multicomponent hydrogels. This crosslinking agent molecule is a high-molecular linear molecule of at least two linearly bonded components, and in particular covalently conjugated components according to the invention, specifically at least one polymer component, a preferably high-molecular component, and at least one peptide component, preferably a low-molecular component. According to the invention, the crosslinking agent molecule has a total molecular weight of 3 kDa or more, preferably 5 kDa or more, in particular 3 kDa to 60 kDa or 5 kDa to 60 kDa.

In conjunction with the invention, a "two-component or multicomponent hydrogel" is understood to be a structure composed of crosslinking agent molecular components and different high-molecular polymer components, in which the polymers are crosslinked with one another via the crosslinking agent molecules to form a gel. The crosslinking takes place preferably via covalent conjugation reactions each with complementary bond functions of the crosslinking agent molecules and the polymer molecules to be crosslinked.

The invention thus provides a linear high-molecular crosslinking agent molecule for two-component or multicomponent hydrogels, wherein the spacing of the bond functions, which are localized on or in the area of the respective molecular terminus, is greatly increased in comparison with known crosslinking agent peptides. The molecular weight of the linear molecule serves as a measure of the distance of the bond functions which are essentially terminal.

The inventors have surprisingly discovered that by using the high-molecular polymer crosslinking agent according to the present invention, the concentration of the crosslinking agent required to form a two-component or multicomponent hydrogel can be reduced significantly in comparison with known peptide polymer crosslinking agents. The concentration required to form a gel is advantageously reduced by a factor of at least 2, preferably by a factor of at least 3, especially preferably by a factor of at least 10 in comparison with the peptide polymer crosslinking agents known from the prior art. An inventive polymer crosslinking agent will form stable hydrogels at concentrations of the bond functions of approx. 3 mmol/liter, based on the hydrogel. It has further been discovered that the efficiency of the crosslinking is also improved with respect to the rate of the crosslinking reaction.

Without being bound to a theory, the invention makes use of the finding that the frequency of the event, wherein the crosslinking agent bonds repeatedly to the same polymer and therefore is no longer available for crosslinking with another polymer molecule decreases with an increase in the molecular spacing of the bond functions in the crosslinking agent molecule involved in the crosslinking. The bond functions in the high-molecular crosslinking agent molecule according to the invention are spaced a distance apart, such that in a comparatively larger number of cases, a crosslinking agent molecule will crosslink at least two different polymer molecules and will thus contribute toward the crosslinking of the polymer molecules to form the gel.

The reduced concentration of the crosslinking agent advantageously make it possible to make available hydrogels having a higher water content than would be possible with known crosslinking agents, in particular with known peptide crosslinking agents. Alternatively or additionally, it is also possible to introduce additional soluble components, especially media components for the cell culture and/or other reagents in a different composition and/or a different concentration, preferably a higher concentration, into the hydrogels, which is impossible with known hydrogels due to the high concentration of traditional crosslinking agents prevailing there, and thus has a negative effect.

The invention also provides a novel teaching for obtaining such advantageous high-molecular crosslinking agents according to the invention by a simple and thus economical method. To produce the high-molecular crosslinking agents according to the invention, the invention provides that an essentially short-chain, i.e., low-molecular peptide component is intramolecularly linked to a high-molecular polymer component. The invention advantageously completely avoids the known complex synthesis of a longer chain peptide to achieve the high molecular weight of the crosslinking agent according to the invention and thus the favorable large spacing of the bond functions in the area of the molecular termini. At this point, the invention provides for the incorporation of one or more preferably high-molecular polymer components into the crosslinking agent molecule.

The crosslinking agent according to the invention may advantageously replace known crosslinking agent molecules having known bond functionalizations, so that the established crosslinking reactions to produce two-component or multi-component hydrogels with peptide crosslinking can still be performed in a known manner. No further adjustment of the chemical linkage is needed and the hydrogels obtained are at least equivalent to those obtained with the crosslinking agent molecules known in the past.

The invention also relates to use in crosslinking agent compositions together with traditional polymer crosslinking agents in which the crosslinking agent molecules according to the invention are contained in amounts that achieve the advantageous effects in the crosslinking agent compositions presented here. Those skilled in the art can readily determine the amount of crosslinking agent molecules of the crosslinking agent composition as a function of the desired intensity of effect. One variant of the invention provides crosslinking agent compositions in which crosslinking agent molecules according to the invention are present in amounts of 10% to 50%, based on the molar amount.

In conjunction with the invention, a "polymer component of the crosslinking agent molecule" is understood to be a preferably high-molecular, preferably linear unbranched molecule, which is composed of simple low-molecular monomers. This is to be differentiated from the "peptide component of the crosslinking agent molecule," which is a preferably low-molecular polyamino acid molecule having a sequence of preferably different amino acids.

In a preferred embodiment of the invention, the polymer component of the polymer crosslinking agent has a molecular weight corresponding essentially at least to the molecular weight of the peptide component or being greater than that; the ratio of the molecular weight of the peptide component to the molecular weight of the polymer crosslinking agent is from 1:1 to approx. 1:20 or more preferably 1:5 to 1:10 or 1:5 to 1:20. The polymer molecule of the crosslinking agent preferably has a molecular weight that is higher in comparison with the molecular weight of the peptide molecule of the crosslinking agent by a factor of at least 2, preferably by a factor of 5 or more, especially preferably by a factor of 10 or more. The polymer molecule, preferably a high-molecular molecule of the crosslinking agent preferably has a molecular weight of at least 3 kDa, 4 kDa or more and especially preferably 10 kDa or more. In one variant, the molecular weight is from 3 to approx. 50 kDa; in another variant, it is from 5 to 25 kDa. The peptide molecule of the crosslinking agent preferably has a molecular weight of 5 kDa or less, preferably 3 kDa or less, more preferably 2 kDa or less. In one variant, the molecular weight of the peptide is 300 Da (0.3 kDa) to 5 kDa; in another variant, it is 500 Da (0.5 kDa) to 2 kDa. In an especially preferred embodiment, the peptide component has only a few amino acids, especially three or four or five or more.

In conjunction with the invention the molecular weight, represented in units of Da (Dalton), is used as an equivalence measure for the size or length of the molecules. It is self-evident that 1 Da corresponds to a molecular weight of 1 u.

The at least one polymer component and the at least one peptide component are preferably intramolecularly linked in the crosslinking agent molecule by covalently conjugating bond function pairs. Therefore at least one of the molecular termini of the polymer and peptide components is bond functionalized to enter into a covalent conjugation with a complementary bond function of the respective other component. It is understood that at least one of the bond functions provided on the molecule can be protected by a suitable protective group to suppress self-conjugation of the molecules.

A bond function for intramolecular linkage is preferably a nucleophilic group. The complementary bond function is then an electrophilic function, in particular an electrophilic double bond. Reactions which leave the functional groups of the peptide component on the side chains, on the N and C terminus untouched are preferred. The conjugation takes place by an addition. It is found that such addition reactions advantageously do not produce any departing groups. This makes it possible to eliminate any additional washing steps to eliminate reactants and departing groups that occur in crosslinking reactions from the resulting conjugate. The intramolecular conjugation can therefore advantageously sustain contamination-free physiological conditions for culturing biological cells. Preferred reactants include thiols, for example, thiol structures in amino acids (for example, cysteine) of the peptide component, for coupling to double bonds of maleimides, vinyl-sulfone, acrylates, preferably acrylamide, methacrylate and acrylate or corresponding compounds.

A preferred reaction to form the intramolecular linkage of the components of the crosslinking agent is Michael's addition which is preferably performed on the basis of one or more thiol groups as the first reactant and preferably maleimide, vinylsulfone or acrylates as the second complementary reactant.

Alternative reaction types for intramolecular linkage of the components of the crosslinking agent molecule include substitution, chemoselective ligation, reductive amination, Staudinger ligation and the so-called Click chemistry. Amines which react with carboxyl group or hydroxyl group are the preferred reactants in substitution processes. In the presence of reducing agents the reactants aldehyde groups and amino groups are linked. In chemoselective ligation, thiol and bromacetyl or aldehyde and aminoxy groups are preferred as the reactants. In Staudinger ligation, phosphine groups are preferably linked to azide groups. In so-called Click chemistry, alkyne groups or cyclooctyne groups are linked to azide groups, optionally in the presence of copper. Other bond functions that can also be used for intramolecular linkage of the crosslinking agent components according to the invention include the streptavidin/avidin and biotin bond partners or corresponding bond functions. The invention is not limited to those mentioned above with respect to the intramolecular bond functions. Those skilled in the art will recognize these and other similar bond functions which they can use in a known way in accordance with the area of use of the crosslinking agent molecule to be synthesized.

In one embodiment, the components in the crosslinking agent molecule according to the invention are linked by a thiol-maleimide conjugation. In a first variant of this, the polymer component has a maleimide function in the area of each molecular terminus and the peptide component of the crosslinking agent has a thiol function in the area of the molecular terminus and a maleimide function in the area of the other molecular terminus. In an alternative variant, the polymer component has the thiol function and the peptide component has a thiol function and a maleimide function. The thiol function of the peptide component is preferably implemented by a cysteine radical. In a first variant the cysteine radical is localized at the C-terminal end. In an alternative variant the cysteine radical is localized on the N-terminal end. A tert-butyl group may be present as the protective group of the thiol function, which is removed to form the intramolecular linkage of the peptide component and the polymer component.

In this preferred embodiment, for intramolecular linkage, the components of the crosslinking agent molecule have the same bond functions or similar bond functions as those which can also be provided on the respective molecular termini of the crosslinking agent molecule and may serve to cross-link bond functionalized polymers in use of the crosslinking agent. This advantageously allows simpler synthesis because a small number of different bond functions must be implemented on the whole. Synthesis of such crosslinking agent molecules is described in greater detail below.

In a preferred variant of the invention, the radical linkage is ruled out as the linkage of the crosslinking agent to the polymer to form the hydrogel; in other words there is no radical linkage to form the hydrogel by means of the polymer crosslinking agent according to the invention. In a preferred embodiment, the invention does not relate to the use of the crosslinking agent molecule to synthesize radically linked single-component gels.

In another preferred embodiment, the components of the crosslinking agent have other bond functions for intramolecular linkage, and these bond functions do not match and are not complementary with the bond functions that are provided on the respective molecular termini of the crosslinking agent molecule and can be used to crosslink bond functionalized polymers in use of the crosslinking agent, to enter into a linkage. This variant is also accessible to a simple synthesis process. In particular protective groups on bond functions to prevent self-conjugation may be omitted. Synthesis of such crosslinking agent molecules is also described below.

In one embodiment of the invention, the crosslinking agent according to the invention has at least one cleavable intramolecular linkage. The invention provides that the at least one cleavable intramolecular bond in the crosslinking agent is localized at least between the bond functions of the crosslinking agent, which are themselves localized in the area of the molecular termini. Therefore, by cleavage of the crosslinking agent, dissolution of the crosslinking of the polymers in the hydrogel and thus a liquefaction of the hydrogel can be achieved. In a first variant of this embodiment, the cleavable link is implemented at the bonding site of the at least one peptide component and the high-molecular polymer component provided according to the invention. In an alternative preferred variant, the cleavable link is implemented within at least one peptide component of the crosslinking agent.

By means of such cleavable bonds, the hydrogel formed with the crosslinking agent according to the invention can be reliquefied by a targeted influence. Such a targeted influence for liquefaction can also emanate from the outside (for example, temperature, radiation) and alternatively or additionally through the action of biological cells cultured in the hydrogel (for example, enzyme action).

In a first embodiment, the cleavable intramolecular bond is a water-cleavable bond which can be cleaved by the influence of and reaction with water. Alternatively or additionally, the cleavable bond may be a bond that is cleavable by the activity of a catalyst. A preferred catalyst is a biological enzyme. Preferred biological enzymes include peptidases and proteinases or in general hydrolases which catalyze hydrolysis of the cleavable bond.

In an alternative or additional embodiment, the cleavable intramolecular bond is a linkage which depends on the pH of the environment and can be cleaved by a change in the pH. In another embodiment, the cleavable intramolecular bond is alternatively or additionally a temperature-dependent linkage, which is cleavable in particular by an increase in temperature. In addition, other linkages which are cleavable by input of energy, in particular electromagnetic radiation, selected from microwaves, light, UV or IR radiation may be provided as the cleavable intramolecular bonds.

In a preferred embodiment, the peptide component of the polymer crosslinking agent has at least one bioactive amino acid sequence. The phrase "bioactive" amino acid sequence is understood to refer to an amino acid sequence or an amino acid pattern that is "recognized" by biological systems, for example, viable biological cells such that at least one component of the biological cell interacts with the bioactive amino acid sequence. Such a component may be an enzymatically active protein. The bioactive amino acid sequence according to the invention is preferably cleavable by a peptide/proteinase activity in particular. Accordingly, the peptide component of the conjugate according to the invention has at least one biocleavable, i.e., enzymatically cleavable, amino acid sequence.

In conjunction with the present invention, matrix metalloproteinases are understood to include in particular collagenases, gelatinases, stromelysins, matrilysins, metalloelastases and membrane metalloproteinases. These proteinases bind to so-called "protein cleavage sites" with a specificity depending on the type of metalloproteinase. Such amino acid sequences are known per se (Nagase and Fields, Biopolymers (Peptide Science), 40 (1996): 399-416).

Tables 1 and 2 show preferred sequence patterns/amino acid sequences of the peptide crosslinking agents listed as preferably cleavable according to the invention. Tables 2 ABCDEF shows sequence patterns arranged according to the respective cleaving metalloproteinases (MPP1-MPP10). It is self-evident that the present invention is not limited to these specific sequences and also includes functional modifications thereof.

TABLE 1

Ac-GCRD-GPQG/IWGQ-DRCG-NH2
Ac-GCRD-GPQG/IAGQ-DRCG-NH2
Ac-GCRD-GDQGIAGF-DRCG-NH2

Ac-GCYK/NRD-CG

NH2-GGGLGPAGGK-NH2
NH2-GGCLGPACGK-NH2

TABLE 1-continued

Dnp-PLGLWA-(D)Arg-NH2

Mca-PLGL-Dpn-(D)Arg-NH2

Mca-KPLGL-Dpa-AR-NH2

TABLE 2

A. MMP1-MMP8

| | |
|---|---|
| Human type I collagen (a1) | Ala-Pro-Gln-Gly$_{775}$~Ile$_{776}$-Ala-Gly-Gln |
| Human type I collagen (a2) | Gly-Pro-Gln-Gly$_{775}$~Leu$_{776}$-Leu-Gly-Ala |
| Human type II collagen | Gly-Pro-Gln-Gly$_{775}$~Leu$_{776}$-Ala-Gly-Gln |
| Human type III collagen | Gly-Pro-Leu-Gly$_{775}$~Ile$_{776}$-Ala-Gly-Ile |
| Human a2-macroglobulin | Gly-Pro-Glu-Gly$_{679}$~Leu$_{680}$-Arg-Val-Gly |
| Rat a,-macroglobulin | Ala-Ala-Tyr-His$_{681}$~Leu$_{682}$-Val-Ser-Gln |
| Rat a2-macroglobulin | Met-Asp-Ala-Phe$_{691}$~Leu$_{692}$-Glu-Ser-Ser |
| Rat a1-macroglobulin | Glu-Pro-Gln-Ala$_{683}$~Leu$_{684}$-Ala-Met-Ser |
| Rat a,-macroglobulin | Gln-Ala-Leu-Ala$_{685}$~Met$_{686}$-Ser-Ala-Ik! |
| Chicken ovostatin | Pro-Ser-Tyr-Phe$_{673}$~Leu$_{674}$-Asn-Ala-Gly |
| Human pregnancy zone protein | Tyr-Glu-Ala-Gly$_{685}$~Leu$_{686}$-Gly-Val-Val |
| Human pregnancy zone protein | Ala-Gly-Leu-Gly$_{687}$~Val$_{688}$-Val-Glu-Arg |
| Human pregnancy zone protein | Ala-Gly-Leu-Gly$_{757}$~Ile$_{758}$-Ser-Ser-Thr |
| a,-Protease inhibitor | Gly-Ala-Met-Phe$_{352}$~Leu$_{353}$-Glu-Ala-Ile |
| Human aggrecan | Ile-Pro-Glu-Asn$_{341}$~Phe$_{342}$-Phe-Gly-Val |
| Human aggrecan | Thr-Glu-Gly-Glu$_{373}$~Ala$_{374}$-Arg-Gly-Ser |
| Human cartilage link | Arg-Ala-Ile-His$_{16}$~Ile$_{17}$-Gln-Ala-Glu |
| Human insulin-like growth factor binding protein-3 | Leu-Arg-Ala-Tyr$_{99}$~Leu$_{100}$-Leu-Pro-Ala |

B. MMP2

| | |
|---|---|
| Guinea pig a 1 (I) gelatin | Gly-Ala-Hyp-Gly$_{547}$~Leu$_{548}$-Glx-Gly-His |
| Rat a I (I) gelatin | Gly-Pro-Gln-Gly$_{190}$~Val$_{191}$-Arg-Gly-Glu |
| Rat a I (I) gelatin | Gly-Pro-Ala-Gly$_{277}$~Val$_{278}$-Gln-Gly-Pro |
| Rat a I (I) gelatin | Gly-Pro-Ser-Gly$_{301}$~Leu$_{302}$-Hyp-Gly-Pro |
| Rat a I (I) gelatin | Gly-Pro-Ala-Gly$_{331}$~Glu$_{332}$-Arg-Gly-Ser |
| Rat a I (I) gelatin | Gly-Ala-Lys-Gly$_{361}$~Leu$_{362}$-Thr-Gly-Ser |
| Rat a I (I) gelatin | Gly-Pro-Ala-Gly$_{382}$~Gln$_{383}$-Asp-Gly-Pro |
| Rat a I (I) gelatin | Gly-Pro-Ala-Gly$_{634}$~Phe$_{635}$-Ala-Gly-Pro |
| Rat a I (I) gelatin | Gly-Pro-Ile-Gly$_{676}$~Asn$_{677}$-Val-Gly-Ala |
| Rat a I (I) gelatin | Gly-Pro-Hyl-Gly$_{685}$~Ser$_{686}$-Arg-Gly-Ala |
| Bovine type I collagen (a1) | Gly-Pro-Gln-Gly$_{775}$~Ile$_{776}$-Ala-Gly-Gln |
| Bovine type I collagen (a2) | Gly-Pro-Gln-Gly$_{775}$~Leu$_{776}$-Leu-Gly-Ala |
| Human aggrecan | Ile-Pro-Glu-Asn$_{341}$~Phe$_{342}$-Phe-Gly-Val |
| Human galectin-3 | Pro-Pro-Gly-Ala$_{62}$~Tyr$_{63}$-His-Gly-Ala |
| Human cartilage link | Arg-Ala-Ile-His$_{16}$~Ile$_{17}$-Gln-Ala-Glu |
| Human cartilage link | Gly-Pro-His-Leu$_{25}$~Leu$_{26}$-Val-Glu-Ala |
| Human insulin-like growth factor binding protein-3 | Leu-Arg-Ala-Tyr$_{99}$~Leu$_{100}$-Leu-Pro-Ala |

C. MMP3

| | |
|---|---|
| Human a2-macroglobulin | Gly-Pro-Glu-Gly$_{679}$~Leu$_{680}$-Arg-Val-Gly |
| Human a2-macroglobulin | Arg-Val-Gly-Phe$_{684}$~Tyr$_{685}$-Glu-Ser-Asp |
| Human a,-antichymotrypsin | Leu-Leu-Ser-Ala$_{360}$~Leu$_{361}$-Val-Glu-Thr |
| a,-protease inhibitor | Glu-Ala-Ile-Pro$_{357}$Met$_{358}$-Ser-Ile-Pro |
| Antithrombin III | Ile-Ala-Gly-Arg$_{385}$~Ser$_{386}$-Leu-Asn-Pro |
| Chicken ovostatin | Leu-Asn-Ala-Gly$_{677}$~Phe$_{678}$-Thr-Ala-Ser |
| Human aggrecan | Ile-Pro-Glu-Asn$_{341}$~Phe$_{342}$-Phe-Gly-Val |
| Substance P | Lys-Pro-Gln-Gln$_{6}$~Phe$_{7}$-Phe-Gly-Leu |
| Human ProMMP-1 | Asp-Val-Ala-Gln$_{80}$~Phe$_{81}$-Val-Leu-Thr |
| Human ProMMP-3 | Asp-Thr-Leu-Gly$_{68}$~Val$_{69}$-Met-Arg-Lys |
| Human ProMMP-3 | Asp-Val-Gly-His$_{82}$~Phe$_{83}$-Arg-Thr-Phe |
| Human ProMMP-8 | Asp-Ser-Gly-Gly$_{78}$~Phe$_{79}$-Met-Leu-Thr |
| Human ProMMP-9 | Arg-Val-Ala-Glu$_{40}$~Met$_{41}$-Arg-Gly-Glu |
| Human ProMMP-9 | Asp-Leu-Gly-Arg$_{87}$~Phe$_{88}$-Gln-Thr-Phe |
| Human fibronectin | Pro-Phe-Ser-Pro$_{689}$~Leu$_{690}$-Val-Ala-Thr |
| Human insulin-like growth factor binding protein-3 | Leu-Arg-Ala-Tyr$_{99}$~Leu$_{100}$-Leu-Pro-Ala |
| | Ala-Pro-Gly-Asn$_{109}$~Ala$_{110}$-Ser-Glu-Ser |
| | Phe-Ser-Ser-Glu$_{176}$~Ser$_{177}$-Lys-Arg-Glu |
| Bovine a 1 (II) collagen, N-telopeptide | Ala-Gly-Gly-Ala$_{115}$~Gln$_{116}$-Met-Gly-Val |
| Bovine a I (II) collagen, N-telopeptide | Gln-Met-Gly-Val$_{119}$~Met$_{120}$-Gln-Gly-Pro |

TABLE 2-continued

| | |
|---|---|
| Bovine a 1 (IX) collagen, NC2 | Met-Ala-Ala-Ser~Leu-Lys-Arg-Pro |
| Bovine a 2 (IX) collagen, NC2 | ~Ala-Lys-Arg-Glu |
| Bovine a 3 (IX) collagen, NC2 | ~Leu-Arg-Lys-Pro |
| Bovine a 1 (XI) collagen, N-telopeptide | Gln-Ala-Gln-Ala~Ile-Leu-Gln-Gln |
| Human cartilage link | Arg-Ala-Ile-His$_{16}$~Ile$_{17}$-Gln-Ala-Glu |
| Bovine insulin, B chain | Leu-Val-Glu-Ala$_{14}$~Leu$_{15}$-Tyr-Leu-Val |
| Bovine insulin, B chain | Glu-Ala-Leu-Tyr$_{16}$~Leu$_{17}$-Val-Cys-Gly |
| D. MMP7 | |
| Human aggrecan | Ile-Pro-Glu-Asn$_{341}$~Phe$_{342}$-Phe-Gly-Val |
| Human cartilage link | Gly-Pro-His-Leu$_{25}$~Leu$_{26}$-Val-Glu-Ala |
| Human prourokinase | Pro-Pro-Glu-Glu$_{143}$~Leu$_{144}$-Lys-Phe-Gln |
| E. MMP9 | |
| Human type V collagen (a1) | Gly-Pro-Pro-Gly$_{439}$~Val$_{440}$-Val-Gly-Pro |
| Human type V collagen (a2) | Gly-Pro-Pro-Gly$_{445}$~Leu$_{446}$-Arg-Gly-Glu |
| Human type XI collagen (a1) | Gly-Pro-Gly-Gly$_{439}$~Val$_{440}$-Val-Gly-Pro |
| Human aggrecan | Ile-Pro-Glu-Asn$_{341}$~Phe$_{342}$-Phe-Gly-Val |
| Human galectin-3 | Pro-Pro-Gly-Ala$_{62}$~Tyr$_{63}$-His-Gly-Ala |
| Human cartilage link | Arg-Ala-Ile-His$_{16}$~Ile$_{17}$-Gln-Ala-Glu |
| F. MMP10 | |
| Human cartilage link | Arg-Ala-Ile-His$_{16}$~Ile$_{17}$-Gln-Ala-Glu |
| Human cartilage link | Gly-Pro-His-Leu$_{25}$~Leu$_{26}$-Val-Glu-Ala |

In an alternative embodiment or preferably an additional embodiment, the bioactive amino acid sequence is a signal sequence, which triggers a biological reaction, in particular being a component of a signal cascade of a biological cell. In an alternative or preferably additional embodiment, the bioactive amino acid sequence is a specific binding sequence.

Essentially known oligopeptides, which can be synthesized by known methods, may be used as the peptide molecule of the crosslinking agent according to the invention. The solid-phase peptide synthesis method is preferred here. The bond functionalization of the peptide can occur as part of the solid-phase peptide synthesis or subsequent thereto. One variant of the specific reaction is explained in the following discussions and examples. In a preferred embodiment, the process of providing the bond functionalized peptide is divided into at least the following substeps: in a first step a polyamino acid molecule having a C-terminal bond function is synthesized de novo, preferably by solid-phase peptide synthesis. In another step the N-terminal end of the synthesized polyamino acid molecule is functionalized with a complementary bond function. It is self-evident that protective groups may be provided to suppress self-conjugation.

Essentially known high-molecular polymers may be used as the high-molecular linear polymer molecule of the crosslinking agent according to the invention. These known high-molecular polymers are preferably selected from linear polymers which have functionalized radicals in particular a hydroxyl group in the area of their respective molecular termini with bond functions. The polymer component is preferably selected from the group consisting of polyethylene glycols (PEG), polypropylene glycols (PPG) and corresponding polymers as well as block copolymers of several thereof such as block copolymers of PPG and PEG. Mixtures of two or more of these polymers may also be considered as the polymer component of the crosslinking agent. One embodiment of the high-molecular polymer component is linear PEG which is functionalized similarly at the end, in particular dithiol PEG and/or dimaleimide PEG.

For crosslinking with the bond functionalized polymer, the crosslinking agent has at least two bond functions, specifically at least one in the area of the two opposing molecular termini of the crosslinking agent. The bond function is preferably in terminal position in particular. In an alternative embodiment, the bond function is in the immediate vicinity of the molecular terminus, in particular one, two, three, four or five monomer units before the molecular terminus. For example, the crosslinking agent molecule has the peptide component in the direction of at least one molecular terminus. The terminal monomer unit, i.e., the terminal amino acid is preferably bond functionalized in this peptide component. Alternatively the second, third, fourth, fifth or sixth amino acid, counting from the molecular terminus, is preferably bond functionalized.

In one variant, two or more bond functions for linking with complementary poly-bond-functionalized polymers are located at the molecular terminus of the crosslinking agent or in the area of the molecular terminus. In one preferred variant, the crosslinking agent has exactly one bond function at each of the two molecular termini.

Bond functions of a polymer crosslinking agent which interact with the complementary bond functions of the polymer to be crosslinked and conjugated with them, preferably covalently, are known per se. Depending on the embodiment of the polymer to be crosslinked, the bond functions characterized above, which can be used according to the invention for intramolecular linkage of the components of the crosslinking agent, are preferably considered for use, depending on the embodiment of the polymer to be crosslinked. A covalent linkage, so-called conjugation of a bond function of the crosslinking agent with a complementary bond function of the polymer to be crosslinked is preferred.

In crosslinking to form hydrogels, it is provided that the polymer molecules to be crosslinked each have at least three or more complementary bond functions. In general, the crosslinking agents according to the invention each have at least two bond functions per molecule, so the polymers to be crosslinked will have at least two complementary bond functions per molecule to enable gel formation due to crosslinking of a plurality of polymers. It is also true that one crosslinking partner has n bond functions per molecule and the other crosslinking partner has m bond functions per molecule, where n+m is at least 5.

The invention also relates to the synthesis of the high-molecular polymer crosslinking agent according to the invention. A crosslinking agent having the bond functions of a first type (A) is synthesized, such that the first component of the crosslinking agent, selected from polymer component and peptide component, is functionalized in the area of the molecular termini of the component each with the bond function of the first type (A) and the other component of the crosslinking agent, selected from peptide component and polymer component, is functionalized with a bond function of the first type (A) in the area of the one molecular terminus of this other component, and is functionalized with a bond function of a second type (B) in the area of the other molecular terminus of this other component, such that the bond function of the second type (B) is complementary to the bond function of the first type (A) and enters into a preferably covalent conjugation with it.

A method is proposed for synthesizing such a crosslinking agent with a bond function of a first type (A), which is localized in the area of its two molecular termini and is suitable for crosslinking of bond functionalized polymer molecules having bond functions of the type (B), which are complementary to the bond functions of the type (A), such that (i) a first component of the polymer crosslinking agent, i.e., either the polymer component or the peptide component, is supplied, having at least bond function of the first type (A) for the crosslinking agent to form the hydrogel at least in the area of one molecular terminus and having a bond function of the other type or the same type (A) for intramolecular linkage of the first component with the other second component of the polymer crosslinking agent, i.e., either the peptide component or the polymer component, in the area of the other molecular terminus. Then (ii) the other second component of the polymer crosslinking agent, i.e., either the peptide component or the polymer component is supplied, having a bond function of the other type or its same type (A) for the intramolecular linkage of the second component with the first component of the polymer crosslinking agent at least in the area of a molecular terminus or both molecular termini and optionally having in the area of the other molecular terminus at least one bond of the first type (A) for the crosslinking reagent for forming the hydrogel. Then (iii) the two components are brought in contact, so that the complementary bond functions in the area of the molecular termini of the first and second components linked together in particular by undergoing conjugation so that a linear conjugate of at least one first component and at least one second component, which is linked to it with a linear bond is formed as the crosslinking agent, such that in the area of the two molecular termini of the conjugate formed from the first and/or second component, at least one bond function of the first type (A) is present for the crosslinking reaction to form the hydrogel. It is self-evident that to suppress self-conjugation, at least one bond function in the component of the conjugate having complementary bond functions at its molecular termini that could conjugate with one another should be present initially in a protected structure such that it s protected by a protective group.

In a first particular embodiment, the invention provides a method comprising or preferably consisting of the following steps: in a first step a first component of the crosslinking agent is supplied, having at least one bond function of the first type (A) in the area of both molecular termini of the component. In a first variant, this first component is the high-molecular linear polymer or in a second variant the peptide.

In addition, the other component of the crosslinking agent according to the invention is supplied. In a first variant, this is the peptide and in the second variant, this is the high-molecular linear polymer. The second component also has at least one bond function of the first type (A) in the area of the first molecular terminus, but has at least one complementary bond function of the second type (B) in the area of its other molecular terminus. The two components are brought in contact, namely under conditions which enable a linear conjugation of at least one of the bond functions of the first type (A) of the first component with at least one of the bond functions of the complementary type (B) of the second component. A linear conjugate of the two components or a conjugate mixture is obtained as the crosslinking agent, having at least one bond function of the first type (A) localized in the area of the two molecular termini of the conjugate thereby synthesized.

The subject matter of the present invention is thus a method comprising the steps:
Supplying a first component having bond functions of the first type (A) localized in the area of their two molecular termini, such that the first component is either (a) a polymer molecule characterized herein or (b) a peptide molecule characterized herein;
Supplying a second component having a bond function of the first type (A) localized in the area of its one molecular terminus and a bond function of the second type (B) localized in the area of its other molecular terminus, such that the second component is the other molecule add to (a) or (b); and
Bringing the first component in contact with the second component under conditions which enable linear conjugation of a bond function of the first type (A) of the first component with the bond function of the second type (B) of the second component, so that a linear conjugate or conjugate mixture with a bond function of the first type (A) localized in the area of each of the two molecular termini of the conjugate is formed as the polymer crosslinking agent.

Thus, a type (A)- and (A)-bond functionalized first component is brought in contact with a type (B)- and (A)-bond functionalized second component to form a type (A)- and (A)-bond functionalized polymer crosslinking agent.

The invention preferably provides that the at least one bond function in the component of the conjugate which have complementary bond functions (A) and (B) on their molecular termini which can even conjugate with one another, are initially present in protected form to prevent bonding within the component (self-conjugation). In the step of providing the first component, the one bond function is preferably provided with or has a protective group to suppress self-conjugation. Then preferably after bringing this component in contact with the other component, i.e., after the conjugate has been formed, the protective group is removed from the one bond function of the first component. In a first embodiment of the invention, the first component of the crosslinking agent is the peptide molecule. It preferably has the bond function of the first type (A) on its one molecular terminus and has the complementary bond function of the second type (B) on its other molecular terminus. In one variant the bond function of the first type (A) is protected by a protective group. In one variant thereof, the bond function of the first type (A) is a thiol function. In this variant, the thiol function is protected by a protective group in a manner which is known per se. The protective group is preferably a tert-butyl group.

In this embodiment of the invention, a conjugate according to the invention is obtained, having a bond function on the respective molecular terminus, such that said bond function is selected from a nucleophilic group which is also used in the intramolecular conjugation reaction and the electrophilic double bond. If a maleimide function and a thiol function are used as the complementary bond function pair for intramolecular conjugation between the polymer molecule and the peptide molecule, then the conjugate according to the invention will have either a thiol function or a maleimide function on each of its molecular termini. With the crosslinking agent according to the invention, it is possible to crosslink polymers that have been functionalized with the corresponding complementary bond function.

The invention also relates to crosslinking agents which can be synthesized by the processes according to the invention described herein and/or can be synthesized directly by these methods. These methods are characterized in greater detail here.

The invention also comprises a polymer crosslinking agent, which is a conjugate mixture of conjugates formed in the conjugation reaction of the high-molecular polymer component with the peptide component in different molar ratios of the starting components. A first conjugate obtainable as a component of the conjugate mixture consists of a polymer component and a peptide component in a molar ratio of 1:1. Another conjugate consists of a polymer component and a peptide component in a molar ratio of 1:2. Another conjugate consists of a polymer component and a peptide component in a molar ratio of 2:1.

In one variant of this embodiment, the resulting crosslinking agent mixture additionally also contains the unconjugated bond functionalized high-molecular polymer component. The amount of unconjugated component in the product mixture depends on the stoichiometric ratio of the starting materials used. In a preferred variant, the starting materials are used in an equimolar ratio. The product mixture accordingly contains approx. one third conjugates with an equimolar ratio of peptide and polymer components to another third of conjugates in which two peptide components are conjugated with a polymer component and, as the last third, the unconjugated polymer component. All three components of the product mixture have in common the fact that they have the same bond functionalization on the respective molecular terminus and may each serve as crosslinking agents. It is self-evident that in the exemplary embodiment cited here, a crosslinking agent molecule embodied according to the first variant of the synthesis process is the starting point. However, the polymer component and peptide component are interchangeable according to the second variant of the process without thereby departing from the teaching of the invention presented here.

The biocleavability provided for in one variant of the invention is ensured only in those crosslinking agents having a cleavable component. The cleavability of the hydrogel produced in this way is a function of the amount of cleavable crosslinking agent molecules and in particular of the ratio of cleavable crosslinking agent to noncleavable crosslinking agent. It is therefore self-evident that the amount of unconjugated polymer component in the crosslinking agent mixture synthesized must not exceed a certain amount in order not to have a negative effect on the biocleavability of the hydrogen crosslinked with it. It is preferably provided that the amount of unconjugated polymer component in the crosslinking agent mixture amounts to 50% or less, preferably 33% or less.

In an alternative second especially preferred embodiment, the components in the crosslinking agent molecule according to the invention are intramolecularly bonded by a different crosslinking reaction than that used for crosslinking with a bond functionalized polymer. In this embodiment, a first component of the crosslinking agent is supplied, having at least one bond function of the first type (A) localized in the area of its one molecule terminus and at least one bond function of the third type (C) localized in the area of its other molecular terminus, the third type not entering into any linkage with the first type (A). Self-conjugation within this component can therefore be prevented. In a first variant, this first component of the crosslinking agent is the high-molecular linear polymer; in an alternative second variant, this first component is the peptide.

A second component, which has at least one bond function of a fourth type (D) localized in the area of its two molecular ends is supplied, such that the bond function of this fourth type (D) is complementary to the bond function of the third type (C) but cannot enter into any linkage with the first type (A). In the first variant, the second component is the peptide; in the second variant, the second component is the high-molecular linear polymer.

The first component is brought in contact with the second component under conditions which enable linear conjugation of the bond function of the third type (C) of the first component with the bond function of the fourth type (D) of the second component. A linear conjugate and optionally a conjugate mixture, each with a bond function of the first type (A) localized in the area of the two molecular termini are formed. The combination of the third type (C) with the fourth type (D) serves only the purpose of intramolecular linkage; bond functions of the first type (A) are not involved in the intramolecular linkage of the component of the crosslinking agent molecule.

Accordingly, the subject matter of the present invention is a method comprising the following steps:
  Supplying a first component having a bond function of the first type (A) localized in the area of its one molecular terminus and a bond function of a third type (C) localized in the area of its other molecular terminus, such that the first component is either (a) a polymer molecule characterized herein or (b) a peptide molecule characterized herein;
  Supplying a second component having bond functions of a fourth type (D) localized in the area of its two molecular termini, this type being complementary to the bond function of the third type (C), such that the second component is the respective other molecule according to (a) or (b); and
  Bringing the first component in contact with the second component under conditions which enable linear conjugation of the bond function of the third type (C) of the first component with the bond function of the fourth type (D) of the second component, so that a linear conjugate with a bond function of type (A) localized in the area of the molecular termini of the conjugate is formed as the polymer crosslinking agent.

Thus a type (A) and (C) bond functionalized first component is brought in contact with a type (D) and (D) bond functionalized second component to form the type (A) and (A) bond functionalized polymer crosslinking agent.

In a preferred variant of the invention, the polymer component has a bond function of a first type (A) in the area of the one molecular terminus, for example, preferably a thiol function, and a bond function of a third type (C), preferably an azide function, for example, in the area of the other molecular terminus. The peptide component has a bond function of the fourth type (D) which is localized at least in the area of both molecular termini and is complementary to the bond function of the third type (C) of the polymer and is, for example, an alkyne function.

In a third especially preferred embodiment, a first component of the crosslinking agent is also supplied, having at least one bond function of the first type (A) localized in the area of its one molecular terminus and at least one bond function of the third type (C) localized in the area of its other molecular terminus. In a first variant, this first component of the crosslinking agent is the high-molecular linear polymer; in an alternative second variant this first component is the peptide.

In addition, however, this additional embodiment supplies a second component, which has at least one bond function of the first type (A) localized in the area of its one molecular terminus and has at least one bond function of the fourth type (D) localized in the area of its other molecular terminus. In the first variant, the second component is the peptide; in the second variant, the second component is the high-molecular linear polymer.

The first component is brought in contact with the second component under conditions which enable linear conjugation of the bond function of the third type (C) of the first component with the bond function of the fourth type (D) of the second component. A linear conjugate with a bond function of the first type (A) localized in the area of the two molecular termini of the conjugate is thus formed. The bond between the third type (C) and the fourth type (D) serves exclusively for intramolecular linkage; bond functions of the first type (A) are not involved in the intramolecular linkage of the component of the crosslinking agent molecule.

The subject matter of the invention is thus a method comprising the steps:
Supplying a first component, which has a bond function of the first type (A) localized in the area of one molecular terminus and a bond function of a third type (C) localized in the area of its other molecular terminus, such that the first component is either (a) a polymer molecule characterized herein or (b) a peptide molecule characterized herein;
Supplying a second component with a bond function of a fourth type (D) which is localized in the area of its two molecular termini and is complementary to the bond function of the third type (C), such that the second component is the respective other molecule according to (a) or (b); and
Bringing the first component in contact with the second component under conditions which enable linear conjugation of the bond function of the third type (C) of the first component with the bond function of the fourth type (D) of the second component so that a linear conjugate with a bond function of the first type (A) is formed in the area of the molecular termini of the conjugate as the polymer crosslinking agent.

Thus, a type (A) and (D) bond functionalized first component is brought in contact with a type (C) and (D) bond functionalized second component to form the type (A) and (A) bond functionalized polymer crosslinking agent.

In a preferred variant of the present invention, in the area of the one molecular terminus, the polymer component has a bond function of the first type (A), preferably a thiol function, for example, and has in the area of the other molecular terminus a bond function of the third type (C), preferably an azide function, for example. In the area of the one molecular terminus, the peptide component has a bond function of the first type (A), preferably a thiol function, for example, and has a bond function of the third type (D), preferably an alkyne function, for example, in the area of the other molecular terminus.

According to these alternative embodiments, the invention preferably supplies a crosslinking agent, such that the peptide component and the polymer component are intramolecularly bonded via a bond function of a type (C) and a type (D), preferably via the linkage of an azide function with an alkyne function, for example. Bond functions of type (A) which can be linked to complementary bond functions of type (B) in the subsequent use for crosslinking of bond functionalized polymers are localized on the respective molecular terminus of the crosslinking agent.

It is self-evident that in addition to the aforementioned specific embodiments, additional embodiments which those skilled in the art can readily derive from this are also conceivable. Mixtures of differently bond functionalized first or second components may also be used in particular. One example of this is a mixture of a type (A) and (D) bond functionalized first component and a type (A) and (C) bond functionalized is brought in contact with a type (C) and (D) bond functionalized second component to form the type (A) and (A) bond functionalized polymer crosslinking agent.

It is self-evident in particular that in a first variant, the first component of the polymer crosslinking agent may be the peptide component, and in a second variant, it may also be the polymer component, such that in this first variant, the second component of the polymer crosslinking agent is the polymer component, and in the second variant, the second component is the peptide component, although the present invention is illustrated herein only on the basis of one of the two variants as an example.

In addition, the invention relates to methods for synthesis of a hydrogel. This method comprises or consists of at least the following steps: first, a polymer crosslinking agent according to the invention or one that can be synthesized or is synthesized according to the invention is supplied. Alternatively, the steps of the methods characterized above are performed to synthesize the polymer crosslinking agent according to the invention. In addition, a complementary bond functionalized polymer is supplied. In this method, the polymer crosslinking agent is brought in contact with the polymer, namely under conditions which enable conjugation of the bond function of the polymer crosslinking agent with the bond functions of the polymer complementary thereto, thus forming a hydrogel of crosslinked polymer.

A polymer used to produce the hydrogel is preferably selected from the group of polymer consisting of polyethylene glycol (PEG), polypropylene glycol (PPG), polyvinyl alcohol (PVA), polyvinyl pyrrolidone (PVP), dextran, pullulan, methyl cellulose, amylose, amylopectin, glycogen and albumins, especially serum albumins and mixtures of two or more thereof. PEG is an especially preferred polymer. PVA is an alternative polymer that is especially preferred. Dextran is another preferred polymer. Serum albumin or serum protein, which can crosslink to form especially biocompatible and biomimetic hydrophilic gels are preferred in particular. The serum albumin and/or serum protein is/are preferably obtained from mammals by an essentially known process, preferably in particular from the human body (human blood serum) or from bovine serum. Maleimide-modified bovine serum albumin is one preferred functionalized polymer that can be used as a crosslinking agent molecule in conjunction with the linear conjugate according to the invention. Those skilled in the art will know of other polymers, in particular hydrophilic polymers that can be used in bond functionalized form with the crosslinking agent to form a hydrogel and are biocompatible if the use of the hydrogel in conjunction with biological cells or tissues is desired.

It is self-evident that the invention is not limited to this application in biocompatible hydrogels. There are additional applications in the fields of physical and chemical analysis and in preparative chemistry.

The subject matter of the invention is also the use of the polymer crosslinking agent according to the invention to reduce the crosslinking agent concentration in the hydrogel produced. One particular aspect of the invention is the use of the crosslinking agent to increase the water content in the hydrogel.

The subject matter of the invention is also a hydrogel that can be produced by the aforementioned methods and/or is produced directly with such methods. The subject matter of the invention is also a hydrogel containing the polymer crosslinking agent according to the invention bound in it, preferably in an amount of 10 mmol/liter or less, preferably 3 mmol/liter to 10 mmol/liter based on the hydrogel. In a first variant the hydrogel does not contain any other crosslinking agent components. In a preferred embodiment, the gel-forming components of the hydrogel are limited to functionalized polymer and the crosslinking agent of the polymer according to the invention.

In another variant, the hydrogel also contains other crosslinking agent components in addition to the crosslinking agent according to the invention. In this variant, the hydrogels are preferably produced by crosslinking with crosslinking agent compositions containing the crosslinking agent according to the invention in addition to at least one other crosslinking agent component. A crosslinking agent composition may contain a traditional polymer crosslinking agent such as dithio-PEG in addition to the crosslinking agent molecule according to the invention.

The hydrogels are especially suitable for culturing, in particular autologous, allogeneic or xenogeneic cells, especially primary cells, in particular mesenchymal stem cells which can differentiate therein through suitable means to form cartilage cells, for example, especially chondrocytes. However the invention is not limited to the use for culturing such cells. These cells include in general primary cells such as somatic stem cells or somatic cells reprogrammed to pluripotent cells ("induced pluripotent stem cells" (ips)) as well as cell lines. One particular area of use is also in tumor cells, which can migrate in the preferably cleavable hydrogel.

These also include, for example, fibroblast cells which develop the morphology typical of fibroblasts, optionally with the use of additional biomodulators and growth factors. The inventors have surprisingly discovered that culturing of fibroblasts cells in hydrogels produced according to the invention supports differentiation into the typical morphology of fibroblasts and/or sustains the differentiation status over the duration of culturing.

The hydrogel according to the invention or that can be produced according to the invention is preferably in the form of a cell culture matrix, preferably biocleavable, or a culture gel.

The subject matter of the invention is also the use of the polymer crosslinking agent according to the invention as a component of the hydrogel for culturing cells.

The subject matter of the invention is also the use of the polymer crosslinking agent according to the invention as a component of a kit for producing a hydrogel, in particular for culturing cells wherein the kit also contains at least the polymer to be crosslinked in addition to the polymer crosslinking agent.

DRAWINGS

The invention is described in greater detail below on the basis of examples and the respective figures although these are to be understood as not restricting the scope of the invention:

FIG. 1ABC show schematic diagrams of the strategy for synthesis of the linear conjugates according to the invention. These figures illustrate schematically the reaction of equimolar quantities of peptide components and polymer components:

According to FIG. 1A, a high-molecular linear polymer (200) is supplied as the polymer component of the crosslinking agent (300). The high-molecular linear polymer has at least one bond function of the first type (A) (210) in the area of both molecular termini. In addition, a peptide (100) is supplied as the peptide component. This has a bond function of the first type (A) (110) in the area of its first molecular terminus and a bond function of the complementary second type (B) (120) in the area of its other molecular terminus. The bond function of the first type (A) (110) is initially protected by a protective group to prevent self-conjugation with the complementary bond function of type (B) (120). The polymer component (200) and the peptide component (100) are brought in contact under conditions which enable linear conjugation of a bond function of the first type (A) (210) of the polymer (200) with the bond function of the complementary second type (B) (120) of the peptide (100) so that a linear conjugate (300) or a conjugate mixture (300) with a bond function of type (A) localized in the area of the two molecular termini of the conjugate (300) thereby synthesized is formed as the crosslinking agent.

According to FIG. 1B, a high-molecular linear polymer (500) is supplied as the polymer component of the crosslinking agent which is equipped with a bond function of the first type (A) (510) localized in the area of the one molecular terminus and with a bond function of the third type (C) (530) localized in the area of the other molecular terminus. The bond function of the third type (C) (530) is not complementary with the bond function of the first type (A) (510) and cannot enter into any linkage or form a conjugate with it. In addition, a linear peptide (400) is supplied as the peptide component, which is furnished with a bond function of a fourth type (D) (440) localized in the area of its two molecular termini wherein the bond function of the fourth type (B) (440) is complementary to the bond function of the third type (C) (530). The polymer component (500) is brought in contact with the peptide component (400) under conditions which enable linear conjugation of the bond function of third type (C) (530) of the polymer (500) with the bond function of the fourth type (D) (440) of the peptide (400). A linear conjugate (600) with a bond function of type (A) localized in the area of both of the molecule termini of the conjugate (600) is formed as the crosslinking agent.

According to FIG. 1C, the high-molecular linear polymer (500) is supplied as the polymer component of the crosslinking agent according to FIG. 1B. In addition, a linear peptide (700) is supplied as the peptide component, which is furnished with a bond function of the first type (A) (710) localized in the area of the one molecular terminus and with a bond function of the fourth type (D) (540) localized in the area of the other molecular terminus. The polymer component (500) is brought in contact with the peptide component (700) under conditions which enable linear conjugation of the bond function of the third type (C) (530) of the polymer (500) with the bond function of the fourth type (D) (740) of the peptide (700). A linear conjugate (800) with a bond function of type (A) localized in the area of both molecular termini of the conjugate (800) is formed as the crosslinking agent.

FIG. 1D shows a specific embodiment of the method according to FIG. 1A.

The peptide component of the crosslinking agent is preferably synthesized by means of the solid-phase peptide synthesis technique. One variant is the DIC/CI-HOBt coupling method using the reagents diisopropylcarbodiimide (DIC) and hydroxybenzene triazole (HOBT). Peptide synthesis is performed by essentially known methods. The preferred synthesis building blocks are 9-fluorenylmethoxycarbonyl (Fmoc) conjugated amino acids or amino acid derivatives. The synthesis reagents used are Fmoc-3,6-dioxaoctanoic acid and Fmoc-(2,4-dinitrophenyl)diaminopropionic acid. The solid-phase peptide synthesis is preferably performed on a resin carrier such as Sieber resin. A chemically protected thiol function is preferably provided at the C-terminal end. To introduce an N-terminal maleimide function, an N-maleoyl-β-amino acid, for example, N-maleoyl-β-alanine is preferably used. Maleimide functionalization is preferably performed on the peptide immobilized on the peptidyl resin.

In one variant, the peptidyl resin is washed in a solvent series (dichloromethane, dimethyl formamide, dichloromethane and diethyl ether) in an essentially known process and is then dried, preferably in a high vacuum. The peptide is split off from the resin by an essentially known method preferably using a solvent series containing water, triisopropylsilane and trifluoroacetic acid. The peptide is preferably precipitated with diethyl ether and then washed in the solvent. In addition, it is preferably provided that the peptide is dissolved in the solvents, for example, tert-butanol and water, and is preferably then lyophilized. In this way a synthetic peptide whose C-terminal end is provided with a chemically protected thiol function and whose N-terminal end is provided with a maleimide function is obtained.

To synthesize a linear conjugate according to the invention, the synthesized and functionalized linear peptide is brought in contact with the PEG component. The PEG component is a linear PEG having one thiol function on each respective molecular terminus. The peptide component and the PEG component are brought in contact under conditions which enable conjugation and thus the formation of linear conjugates of peptide components and PEG components. Three reaction products are preferably obtained: a first conjugation product contains a PEG component and two peptide components each attach to one end of the PEG component, wherein the maleimide function of the peptide component is conjugated with a terminal thiol function of the linear PEG. The molar ratio of peptide component to PEG component in the linear conjugate is 2:1. Another reaction product is a linear conjugate in which a PEG component is conjugated with a peptide component at one end, namely via the maleimide group of the peptide with the thiol group at one end of the PEG molecule. The molar ratio of peptide component to PEG component in this conjugate is 1:1.

In a preferred variant, the reactants are conjugated in approx. equimolar quantities. The invention provides that the product mixture contains approx. 33% double-conjugated conjugate (molar ratio of peptide component to PEG component 2:1), approx. 33% monoconjugated conjugate (molar ratio of peptide component to PEG component 1:1) and approx. 33% of conjugated dithiol PEG, based on the molar ratios of the components in the conjugation product. Therefore, in a preferred embodiment, the present invention also includes a conjugate mixture, which consists at least of the double-conjugated conjugate and the single-conjugated conjugate and optionally also contains unconjugated dithiol PEG.

Figure 7:
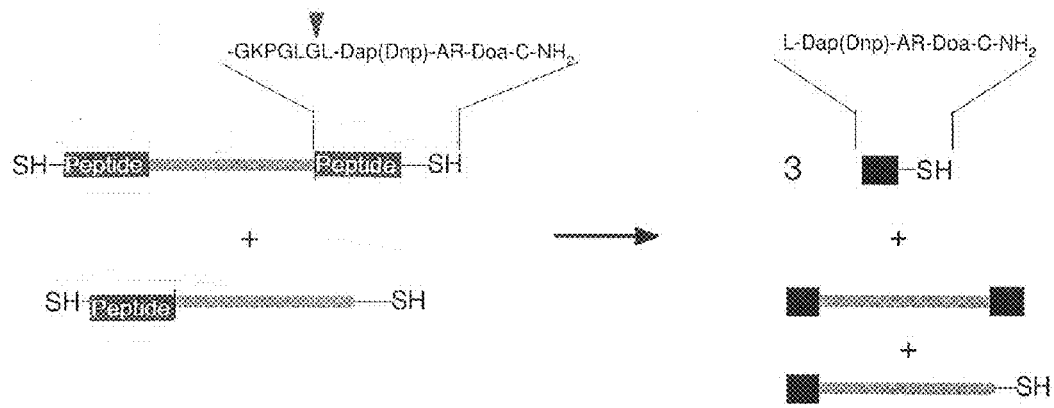

FIG. 7 shows the schematic diagram of the enzymatic degradation of the crosslinking agent according to the invention by matrix metalloprotease (MMP). The tip of the arrow points to the MMP interface in the peptide component. The chromophore Dap(Dnp) remains in the cleaved fragment of the peptide component of the crosslinking agent molecule.

Figure 8:
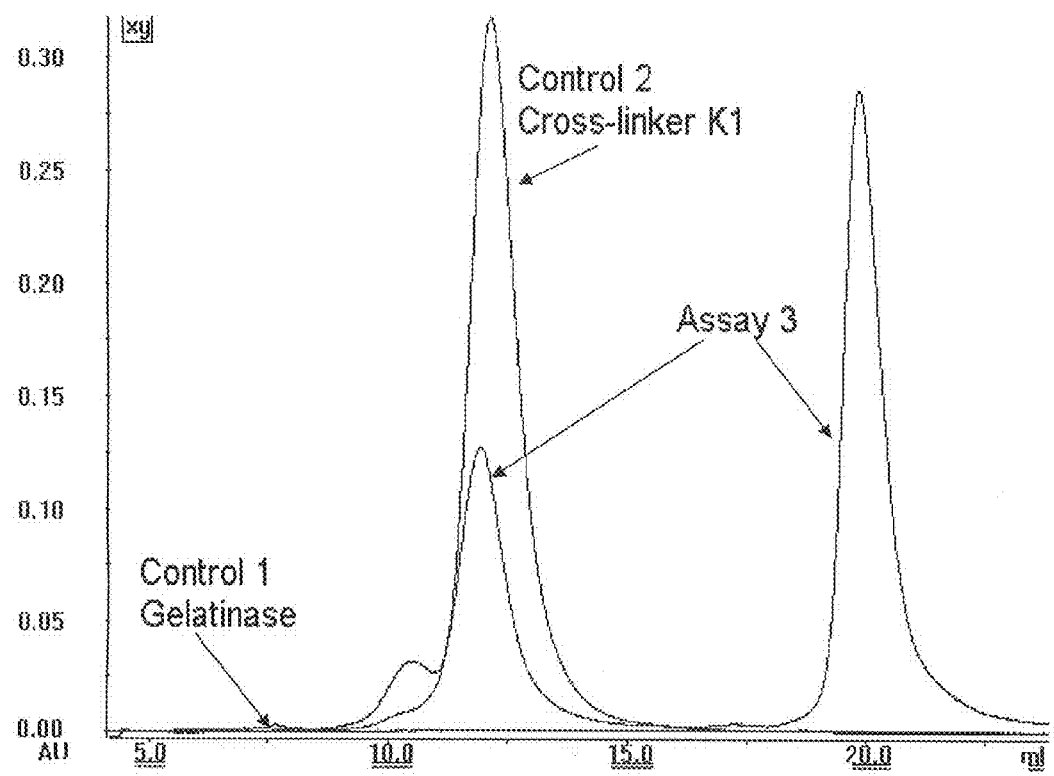

FIG. 8 shows chromatograms at 358 nm after gel filtration of the crosslinking agent molecule according to the invention before MMP2 degradation (control 2) and after MMP2 degradation (assay 3) as well as the enzyme control (control 1). A linear fragment which elutes at approx. 20 mL (assay 3) is split off from the linear conjugate according to the invention by the MMP2 degradation.

Figure 9:
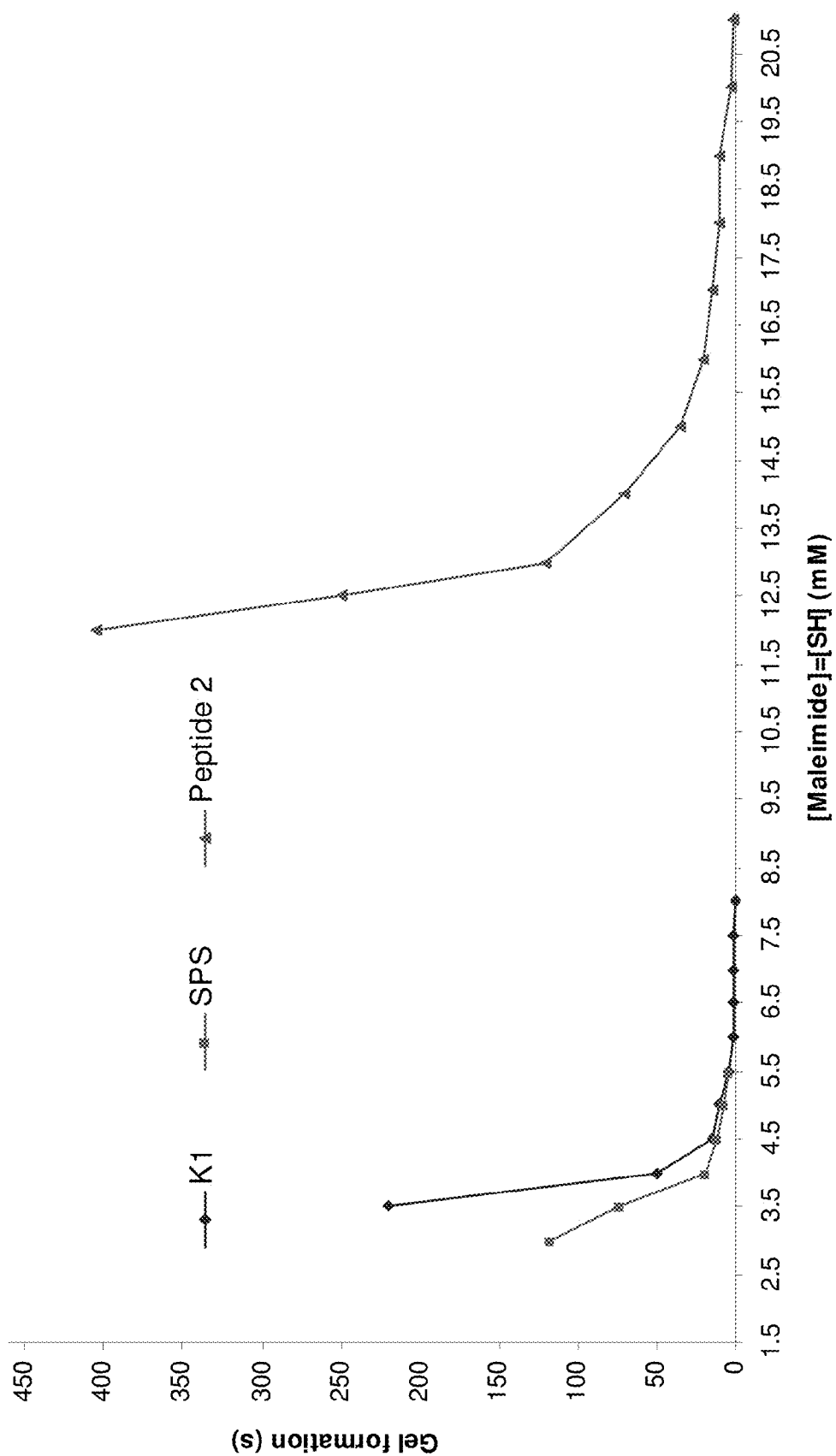

FIG. 9 shows comparative experiments in gel formation using different crosslinking agents and maleimide dextran as the polymer to be crosslinked. The efficiency in gel formation due to the linear conjugate according to the invention as a crosslinking agent is improved by a factor of more than 3 in comparison with the unconjugated low-molecular peptide as the crosslinking agent (legend: K1: linear conjugate according to the invention; SPS: dithiol peptide; peptide 2: low-molecular control peptide with two distal thiol functions (cysteine)).

Figure 10:
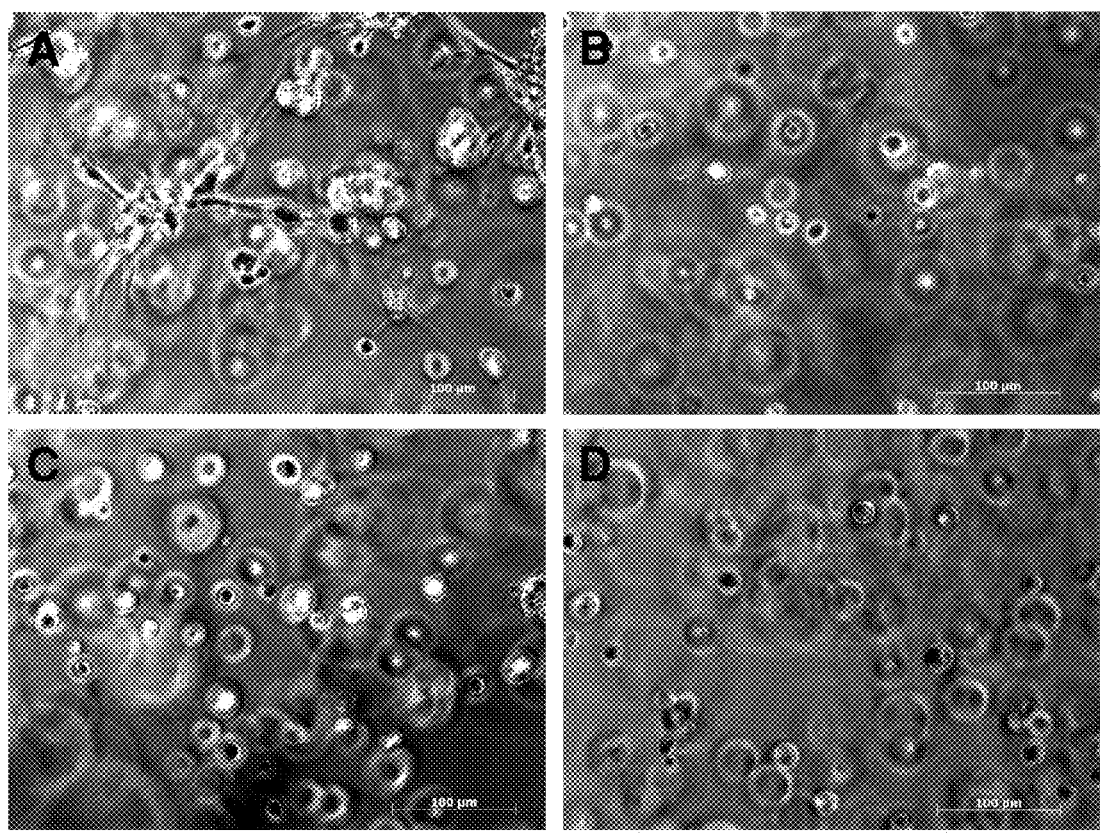

FIG. 10 shows microscopic phase contrast images of fibroblasts (cell line 3T3) in PVA hydrogels after two days in culture. To form the PVA hydrogels, peptide-PEG conjugate according to the invention (10A, C) or PEG (10B, D) as the crosslinking agent is covalently coupled to PVA in the presence of 1 mmol/liter adhesion peptide RGD (10A, B) or 1 mmol/liter thioglycerol (10C, D).

DETAILED DESCRIPTION

Example 1

Synthesis of a Maleimide- and Thio-Functionalized Synthetic Peptide (According to the Invention)

Peptide Mal-GKPLGL-Dap(Dnp)-AR-Doa-Cys(StBu)-$NH_2$ was synthesized as a component of the crosslinking agent molecule according to the invention.

With the help of the DIC/chlorine-HOBt coupling method, a peptide was synthesized on a Sieber resin (Novabiochem) by means of the solid-phase peptide synthesis technique. Fmoc-3,6-dioxaoctanoic acid and Fmoc-(2,4-dinitrophenyl) diaminopropionic acid (Iris Biotech, Marktredwitz, Germany) and Fmoc-L-Arg(Pbf), Fmoc-L-Cys(StBu), Fmoc-Gly, Fmoc-L-Lys(Boc), Fmoc-L-Pro, Fmoc-L-Ala and Fmoc-L-Leu (Merck KGaA, Darmstadt, Germany) were used as the synthesis building blocks. N-maleoyl-β-alanine was used to introduce the N-terminal maleimide group with N,N-dimethyl formamide (Biosolve, Vlakensvaard, Netherlands) as the solvent.

The peptidyl resin was washed with dichloromethane and DMF and then again with dichloromethane and diethyl ether and dried in a high vacuum. Cleavage of the peptide from the resin was performed next using the following mixture: water/triisopropylsilane/trifluoroacetic acid=5/3/92 (v/v/v).

After incubating at room temperature (RT) for 1.5 hours, the peptide was precipitated with diethyl ether, stored for 1 hour at −20° C. and with precipitate was then washed three times diethyl ether. After the last washing step the peptide was dissolved and lyophilized with tert-butanol/water=4/1 (v/v).

Figure 2:
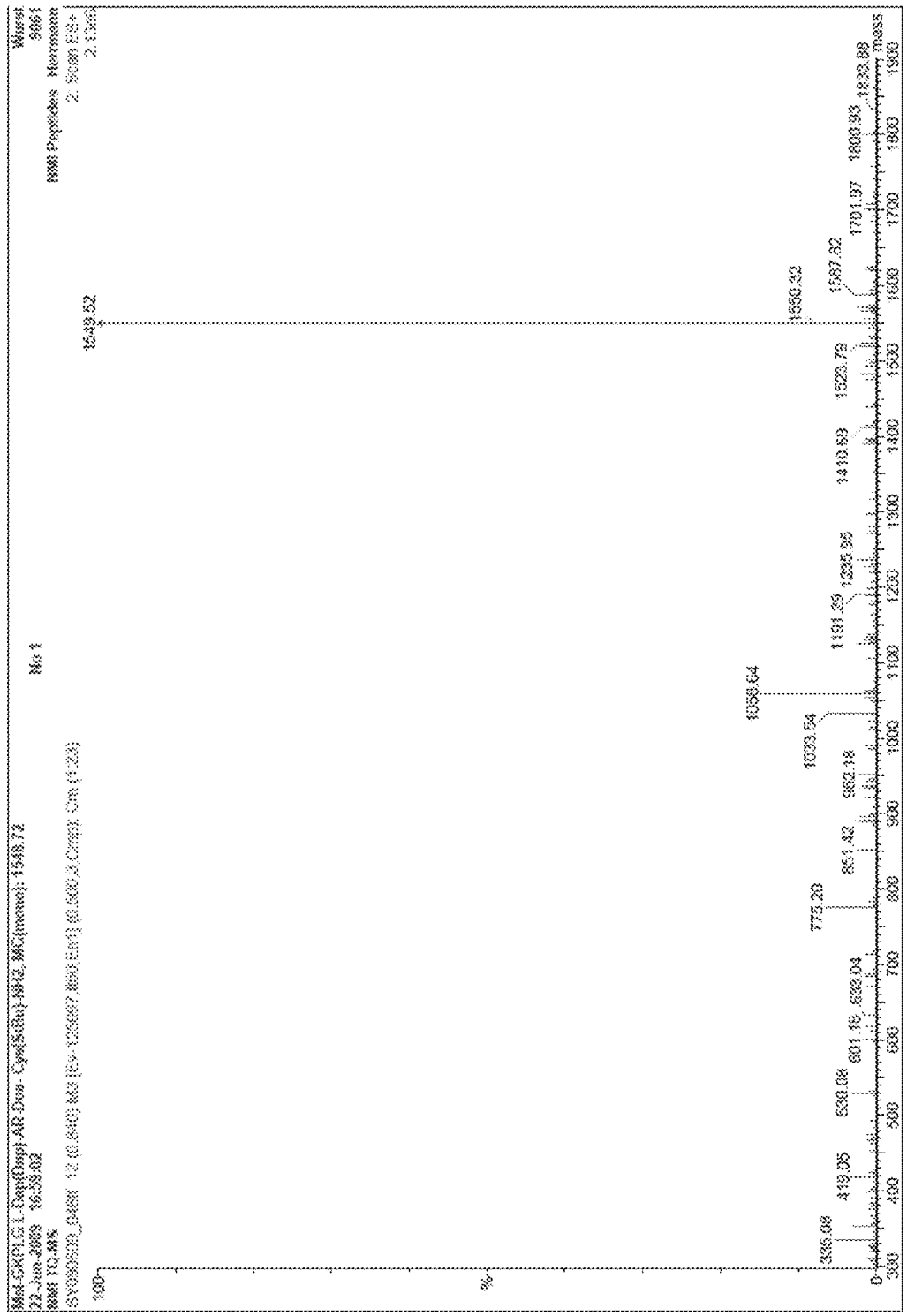
FIG. 2 shows a mass spectrogram of a synthetic peptide used to form the crosslinking agent according to the invention.
Figure 3:
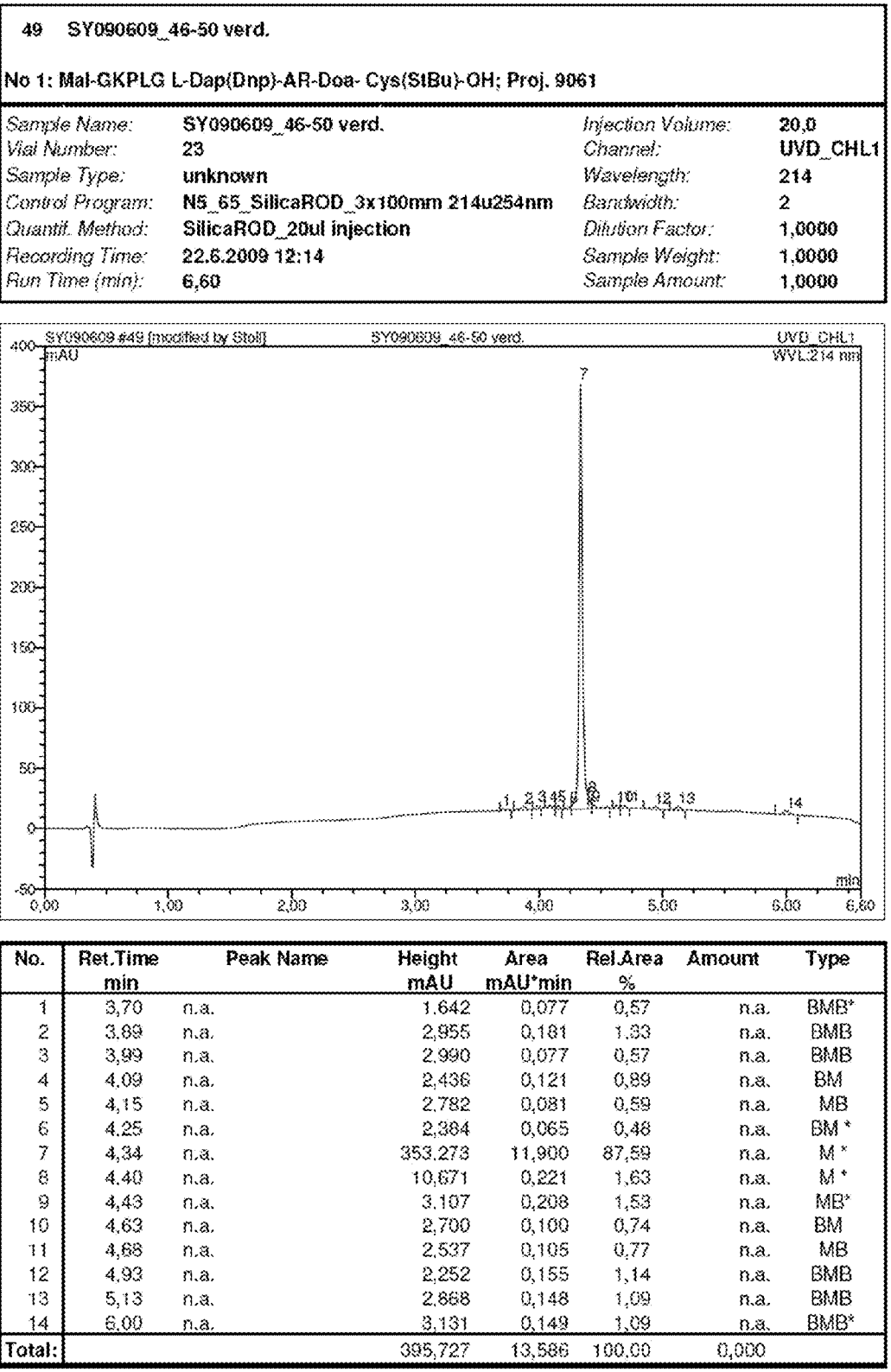
FIG. 3 shows the RP-HPLC analysis of the peptide according to FIG. 2.

The product was characterized by HPLC and mass spectrometry, yielding a purity of 87.6% (detection at 214 nm); the mass found is $[M+H]^+=1549.52$ in comparison with the monoisotopic ideal mass of 1548.72 (FIGS. 2 and 3).

Figure 4:
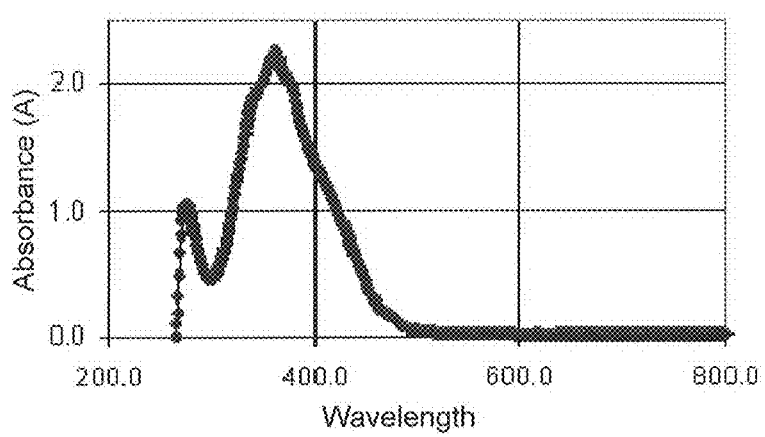
FIG. 4 shows an absorption spectrum in the range of 200 to 800 nm of the peptide according to FIGS. 2 and 3.

Mal-GKPLGL-Dap(Dnp)-AR-Doa-Cys(StBu)-NH$_2$ (peptide 1; 0.39 mg/mL or 214 µmol/L) was analyzed by determining the absorption spectrum at 200-800 nm (FIG. 4). Two peaks were identified at 274 nm and 358 nm. The extinction coefficients of these two absorption bands are $\epsilon(358$ nm$)=10.5$ mmol/L$^{-1}$ cm$^{-1}$ and $\epsilon(274$ nm$)=4.3$ mmol/L$^{-1}$ cm$^{-1}$.

Figure 5:
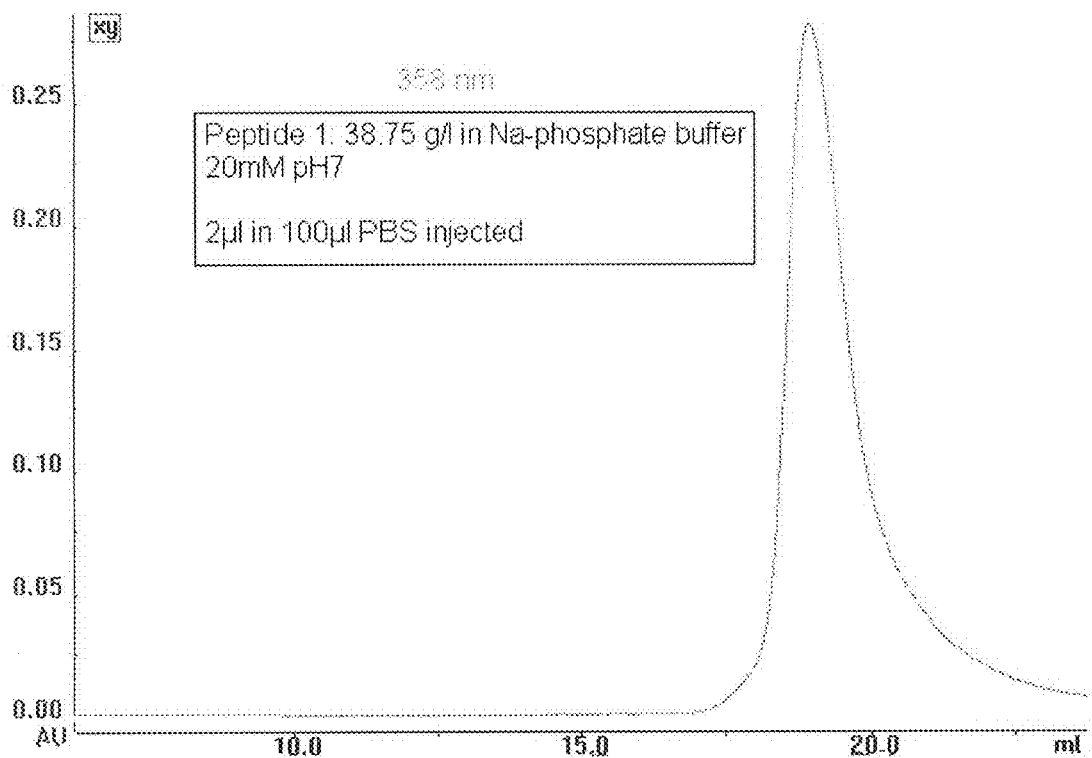
FIG. 5 shows the gel filtration analysis represented as absorption at a wavelength of 358 nm (dinitrophenyl signal (Dap(Dnp))) of the peptide according to FIGS. 2, 3 and 4.

The peptide was also analyzed by gel filtration, measuring the absorption of the eluate at 358 nm in a flow cell (FIG. 5).

Example 2

Synthesis of a Thiol Functionalized Low-Molecular Peptide (Comparative Example)

A low-molecular crosslinking agent peptide Ac-C-Doa-Doa-GKPLGL-Dap(Dnp)-AR-Doa-C—OH was synthesized.

Using PyClock™ as the activator, the peptide was synthesized on a TCP (trityl chloride-polystyrene) resin (Pepchem) loaded with Fmoc-L-Cys(Trt)-OH by means of the solid-phase peptide synthesis technique on a Prelude peptide synthesizer (Protein Technologies Inc., South Coach Drive, Tucson, Ariz., USA). The synthesis building blocks used were Fmoc-3,6-dioxaoctanoic acid and Fmoc-(2,4-dinitrophenyl) diaminopropionic acid (Iris Biotech, Marktredwitz, Germany) as well as Fmoc-L-Arg(Pbf), Fmoc-L-Cys(Trt), Fmoc-Gly, Fmoc-L-Lys(Boc), Fmoc-L-Pro, Fmoc-L-Ala and Fmoc-L-Leu (Merck KGaA, Darmstadt, Germany). The solvent used was N,N-dimethyl formamide (Biosolve, Vlakensvaard, NL). The N-terminal acetyl group was introduced by means of a mixture of acetic anhydride and N-methylmorpholine in NMP.

The peptidyl resin was washed five times with dichloromethane and dried in a stream of nitrogen. Next the peptide was split off from the resin by means of the following mixture: phenol, ethanediol, thioanisole, water, triiso-propylsilane, trifluoroacetic acid=3.35/2.1/3.35/4.2/2.9/84.1 (w/v/v/v/v/v).

After agitating the resin for 2 hours with the aforementioned mixture at RT, the peptide was precipitated with diethyl ether, stored for 2 hours at −20° C. and then the precipitate was washed three times with diethyl ether. After the last washing step, the peptide was dissolved in tert-butanol/water=4/1 (v/v) and freeze dried in a high vacuum.

Characterization of the product by HPLC and mass spectrometry yielded a purity of 83.4% (detection at 214 nm). The mass found is $[M+H]^+=1746.36$ in comparison with the monoisotopic ideal mass of 1745.81.

Example 3

Conjugation of the Maleimide-/Thiol-Functionalized Synthetic Peptide with Dithiol Peg A peptide with a molecular weight of 0.5 kDa to 2 kDa, having a maleimide group at one end and a protected thiol group at the other end is synthesized. Such a peptide is described in Example 1. The peptide is mixed with polyethylene glycol (PEG) with an average molecular weight of 3 kDa to 20 kDa, which has a thiol group at both ends, with approximately equimolar concentrations. Reaction conditions in which one or both thiol groups of the polymer conjugate with the maleimide group of the peptide are selected. Next the protective group on the thiol of the peptide is removed and the conjugate is purified.

Figure 1A:
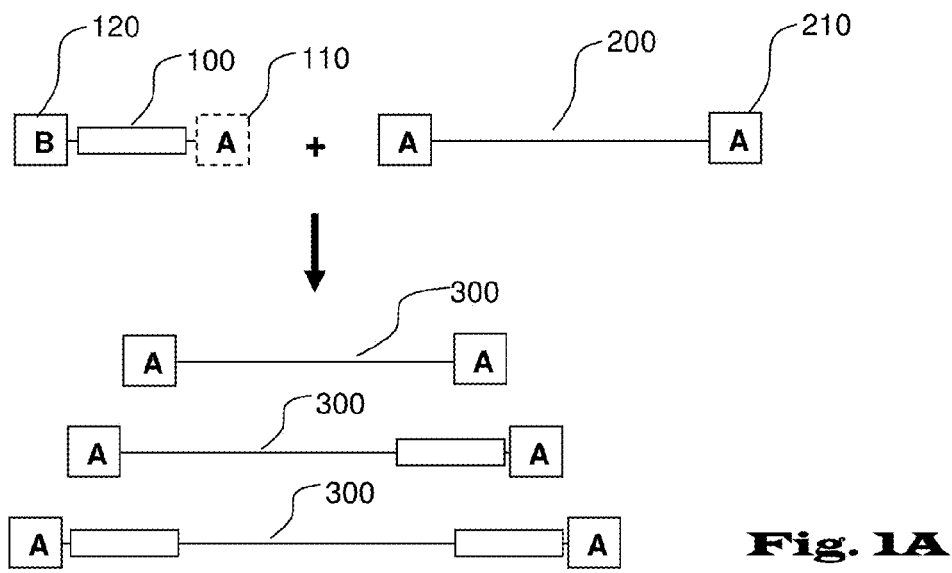
Figure 1B:
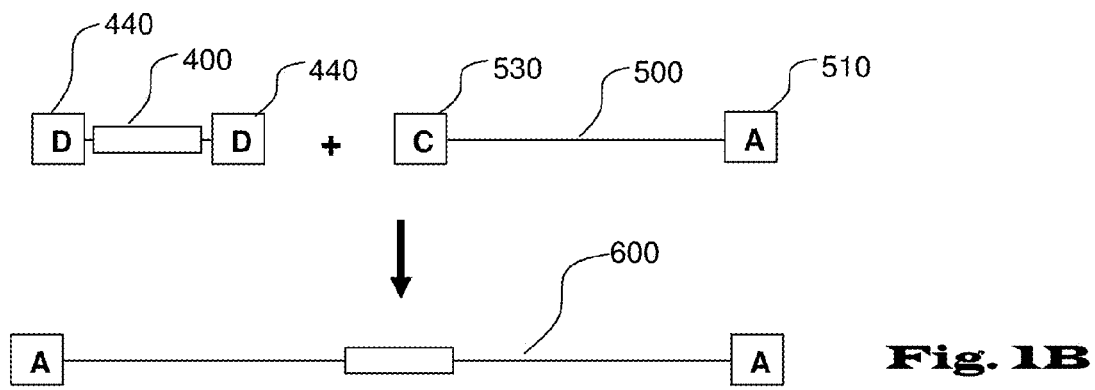
Figure 1C:
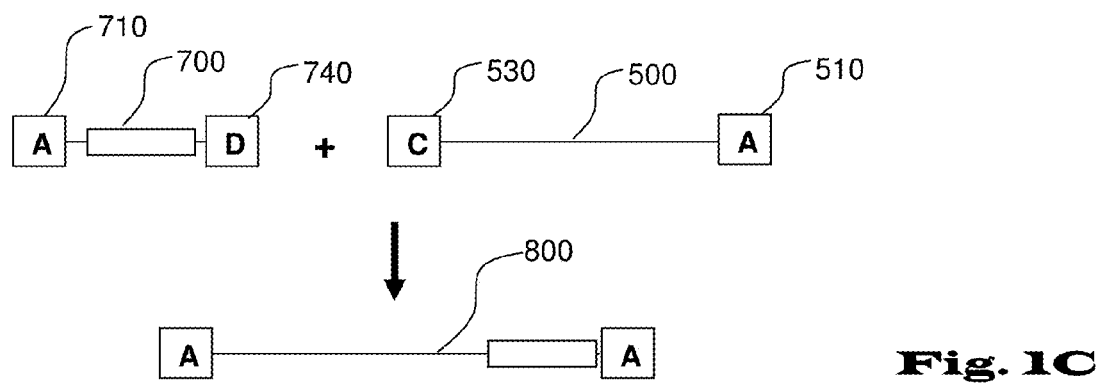
Figure 1D:
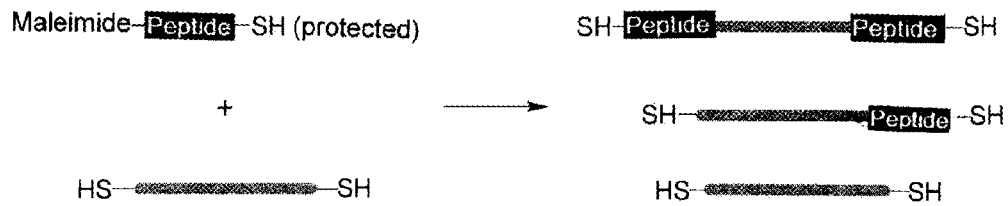

The reaction is diagramed schematically in FIGS. 1A and 1C and explained in the corresponding description of the figures.

Three polymer species are obtained as a result of the reaction:
Thiol-PEG-thiol (no conjugate)
Thiol-PEG-peptide-thiol (1:1 conjugate)
Thiol-peptide-PEG-peptide-thiol (2:1 conjugate)

All three polymers contain two terminal bond functions (here: thiol groups) whose distance from one another is defined by the sum of the molecular weight of the PEG and peptide components.

HS-PEG-SH was analyzed by determining the thiol groups (Ellman test) and by determining the PEG content with polymethacrylate.

Peptide 1 from Example 1 (53.2 mg; 30.4 µmol; 1 equivalent) was dissolved in 3.3 mL ammonium acetate (100 mmol/liter; pH 7.8), mixed with HS-PEG-SH (33.4 µmol SH groups; 1.1 equivalent) and adjusted to a total volume of 5.3 mL with ammonium acetate (100 mmol/L; pH 7.8). After incubating for one hour on ice, a reducing agent (tris(2-carboxyethyl)phosphine (TCEP, 112.5 µmol)) was added to the solution. After 40 minutes more at RT, acetic acid was added to the solution until reaching a pH of 2. This solution was placed in a dialysis tube (MWCO 2000) and dialyzed four times against a phosphate buffer (pH 3) with decreasing concentrations (50 mmol/liter, 2 mmol/liter, 2-mmol/liter and 0.2 mmol/liter phosphate). The dialysate (16.5 mL) was reduced to a volume of 1.84 mL by sublimation, then sterile filtered and stored in aliquots at −80° C.

The concentration and yield of the component of the PEG peptide conjugate (K1) were determined by determining the absorption of Dap(Dnp) (see Example 1) and by determining the PEG content:

| Component: | Peptide | PEG |
| --- | --- | --- |
| Concentration (mmol/L) | 11.4 | 8.7 |
| Substance quantity (µmol) (at 1.84 mL) | 21 µmol | 16 µmol |
| Yield | 69% | 96% |

Figure 6:
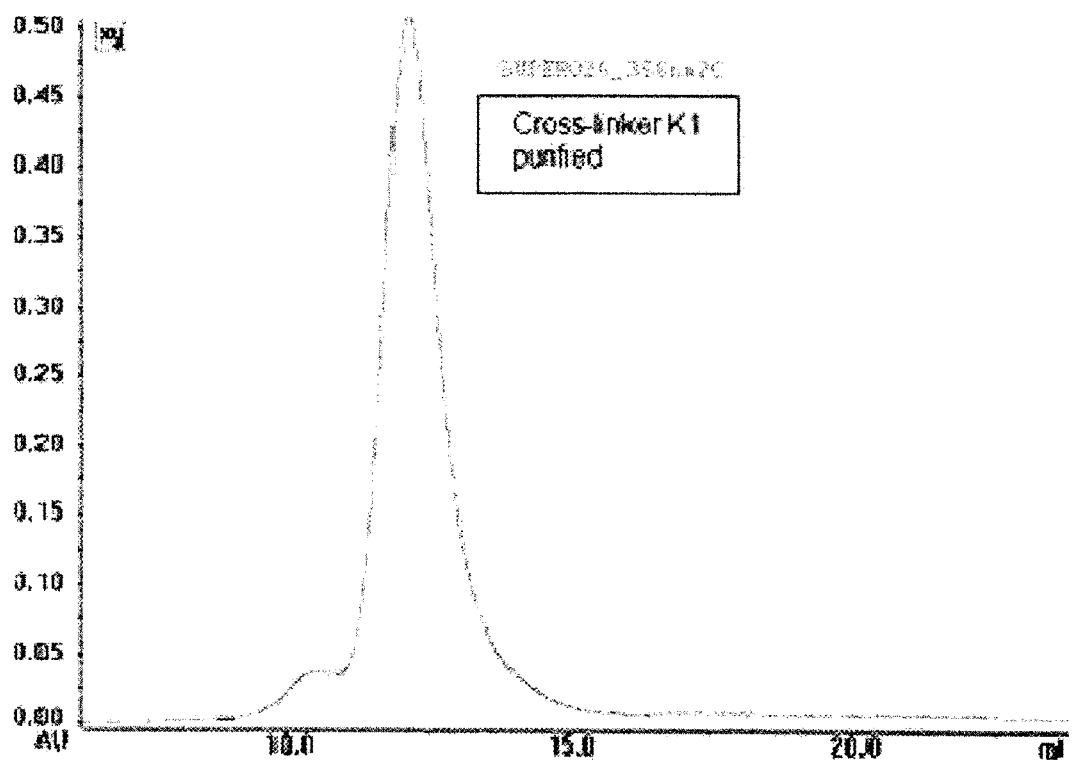
FIG. 6 shows a chromatogram at 258 nm after gel filtration of the linear conjugate according to the invention from the peptide and a PEG component.

K1 was analyzed at 358 nm by gel filtration and by preparing a chromatogram (FIG. 6), showing a shift in the dinitrophenyl signal (Dap(Dnp) from 19 mL (see FIG. 5) for 12.5 mL). The chomophor is thus associated with a much higher molecular weight after the conjugation reaction.

The cleavability of the peptide was tested with MMP2 (gelatinase). To do so, 5 µL of the conjugate was incubated with 2 µL MMP2 (Sigma item no. M9445) in 55 mmol/liter Tris, 1.1 mmol/liter $CaCl_2$, 0.055% Triton X-100, 2.9 mmol/liter TCEP at pH 7.5 in a total volume of 110 µL to enzymatically cleave the conjugate. Based on the positions of the interface for MMP2 with peptide 1 (between glycine and leucine) and of the chromophore, a small peptide fragment should be formed by proteolytic digestion, containing the chromophore (FIG. 7).

To analyze the degradation fragments, the batch was subjected to gel filtration together with controls (enzyme, undigested conjugate) (FIG. 8), using 100 mmol/liter ammonium acetate buffer (pH 4.8) with 0.1 mmol/liter TCEP as the mobile phase to prevent oxidation of the SH groups (FIG. 8). The gel filtration analysis has shown that a smaller fragment which elutes at approx. 20 mL was split off from the conjugate molecule (assay 3 in FIG. 8) by MMP2.

To analyze the formation of the gel, the peptide-PEG conjugate (K1) was compared with two known crosslinking agents, each of which contained two distal thiol groups and had a different molecular weight. The comparative crosslinking agents were Ac-Cys-Doa-Doa-KPLGL-Dpa-AR-Doa-Cys-OH (peptide from Example 2) with a molecular weight of 1746 g/mol and a HS-PEG-SH (10 kDa). All the crosslinking agents were mixed with maleimide-modified dextran in different concentrations, using maleimide groups and thiol groups in equal amounts.

FIG. 9 shows the time until gel formation, which was determined by estimating the viscosity of the batches.

It was found that the conjugate with a molecular weight of approx. 11,500 g/mol, like HS-PEG-SH, forms gels above a reactive group concentration of approx. 3-4 mmol/liter. In contrast with that, the low molecular peptide from Example 2 which contains the same biologically relevant sequence as K1 but is equipped with two distal thiol groups (cysteine) forms gels only above approx. 13 mmol/liter. The efficiency of gel formation by the peptide-PEG conjugate was improved by a factor of more than 3 to 4 in comparison with the unconjugated peptide.

Example 4

In Vitro Culturing of Fibroblasts

Hyrogels with a volume of 30 µL each were prepared, each containing approx. $1.5 \times 10^4$ 3T3 cells. Depending on the composition of the gels, 5 mmol/liter maleimide groups of PVA, 1 mmol/liter RGD peptide (Ac-C-Doa-Doa-GRGDSP-NH2) and/or thioglycerol and an amount of SH groups corresponding to 4 mmol/liter, coupled to the PEG peptide conjugate and/or PEG (10 kDa) as the bond functions, were used. The gels were prepared as described in the exemplary embodiments of DE 10 2007 034 580 A1. The cells that were sown were incubated with DMEM (Dulbecco's Modified Eagle Medium, high glucose), 2 mmol/liter glutamine and 10% fetal calf serum at 37° C. and 5% $CO_2$.

FIG. 10ABCD show the morphology of fibroblasts (cell line 3T3) in PVA hydrogels after two days in culture. FIGS. 10A through 10D show microscopic phase contrast images from the center of the respective gel and illustrate the behavior of the cells in the entire gel representatively. Hydrogels were prepared using MMP cleavable peptide-PEG conjugate (FIGS. 10A, C) or with PEG (FIGS. 10B, D) as the crosslinking reagent. In FIGS. 10A and 10B, 1 mmol/liter of the adhesion peptide RGD was covalently coupled to PVA in the hydrogen and in FIGS. 10C and 10D, 1 mmol/liter thioglycerol was covalently coupled to PVA. The fibroblasts assume a spindle-shaped morphology only when the hydrogels were produced with MMP-cleavable crosslinking agent (peptide-PEG conjugate) and the adhesion peptide RGD (FIG. 10A). The cells remain round when the crosslinking agent (PEG) is not cleavable even if a suitable cell adhesion molecule (RGD) is present in the gel (FIG. 10B). FIG. 10C shows that no spindle-shaped morphology can be formed despite the cleavable crosslinking agent without the adhesion molecule. The cells also remain round in gels without adhesion molecules and a cleavable crosslinking agent (FIG. 10D).

The invention claimed is:

1. A bond functionalized polymer crosslinking agent with bond functions which are localized in an area of a molecular terminus of the crosslinking agent and have at least one peptide component and at least one polymer component bonded thereto to form a linear molecule and having a molecular weight of at least 3 kDa or more, wherein the crosslinking a en includes crosslinking complementary bond functionalized polymers forming one of a two-component hydrogel and a multicomponent hydrogel without any radical linkage.

2. The crosslinking agent according to claim 1, wherein the polymer component of the crosslinking agent has a molecular weight of 3 to 50 kDa.

3. The crosslinking agent according to claim 1, wherein the peptide component of the crosslinking agent has a molecular weight of 0.3 to 10 kDa.

4. The crosslinking agent according to claim 1, wherein the polymer component and peptide component are covalently conjugated in the crosslinking agent.

5. The crosslinking agent according to claim 1, wherein the crosslinking agent is a mixture of compounds wherein the polymer component and the peptide component are bonded in molar ratios of 2:1, 1:1 and/or 1:2.

6. The crosslinking agent according to claim 1, wherein the bond functions for crosslinking are selected from a group of covalent bond functions are selected from a group consisting of carboxyl, hydroxyl, amine, thiol, maleimide, vinylsulfone, methacrylate, acrylate, acrylamide, bromacetyl, aldehyde, amino, aminoxy, phosphine, azide, alkyne and cyclooctyne.

7. The crosslinking agent according to claim 1, wherein the polymer component of the crosslinking agent is selected from PEG, PPG, block copolymers thereof and mixtures of two or more thereof.

8. The crosslinking agent according to claim 1, wherein the crosslinking agent has at least one cleavable intramolecular bond between the bond functions localized in the area of the molecular termini, this cleavable intramolecular bond being selected from the group consisting of water-cleavable compounds, enzyme-cleavable compounds, pH-dependent compounds, temperature-dependent compounds and electromagnetically cleavable compounds.

9. The crosslinking agent according to claim 8, wherein the cleavable bond is an enzyme-cleavable amino acid sequence in at least one peptide component of the crosslinking agent.

10. A hydrogel comprising the crosslinking agent according to claim 1.

11. The hydrogel according to claim 10, wherein a concentration of polymer crosslinking agent is less than 10 mmol/liter of the hydrogel produced.

12. The hydrogel according to claim 10, wherein the hydrogel is a cell culture gel.

13. The crosslinking agent according to claim 1, wherein the crosslinking agent increases the water content in hydrogels.

14. A bond functionalized polymer crosslinking agent with bond functions which are localized in an area of a molecular terminus of the crosslinking agent and have at least one peptide component and at least one polymer component bonded thereto to form a linear molecule and having a molecular weight of at least 3 kDa or more, wherein the crosslinking agent includes crosslinking complementary bond functionalized polymers forming one of a two-component hydrogel and a multicomponent hydrogel, and further wherein the bond functions exclude acrylates.

15. The crosslinking agent according to claim 14, wherein the bond functions are from a nucleophilic group.

16. The crosslinking agent according to claim 14, wherein the bond functions are selected from a group consisting of streptavidin/avidin and biotin bond partners, and corresponding bond functions.

17. A bond functionalized polymer crosslinking agent with bond functions which are localized in an area of a molecular terminus of the crosslinking agent and have at least one peptide component and at least one polymer component bonded thereto to form a linear molecule and having a molecular weight of at least 3 kDa or more, wherein the crosslinking agent includes crosslinking complementary bond functionalized polymers forming one of a two-component hydrogel and a multicomponent hydrogel, and further wherein the bond functions are derived from a side chain of an amino acid residue in the at least one peptide component.

* * * * *